United States Patent
Roy et al.

(10) Patent No.: US 11,887,712 B2
(45) Date of Patent: Jan. 30, 2024

(54) METHOD AND SYSTEM FOR CLASSIFYING DETECTED EVENTS AS LABELED EVENT COMBINATIONS FOR PROCESSING AT A CLIENT APPLICATION

(71) Applicant: MEDTRONIC MINIMED, INC., Northridge, CA (US)

(72) Inventors: Anirban Roy, Agoura Hills, CA (US); Benyamin Grosman, Valley Village, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 345 days.

(21) Appl. No.: 17/120,054

(22) Filed: Dec. 11, 2020

(65) Prior Publication Data

US 2021/0183490 A1  Jun. 17, 2021

Related U.S. Application Data

(60) Provisional application No. 62/948,007, filed on Dec. 13, 2019.

(51) Int. Cl.
*G16H 20/17* (2018.01)
*G16H 20/10* (2018.01)
(Continued)

(52) U.S. Cl.
CPC ............ *G16H 20/10* (2018.01); *A61B 5/1118* (2013.01); *A61B 5/14532* (2013.01);
(Continued)

(58) Field of Classification Search
CPC ........ G16H 80/00; G16H 20/10; G16H 10/40; G16H 50/30; G16H 10/00
See application file for complete search history.

(56) References Cited

U.S. PATENT DOCUMENTS 4,562,751 A  1/1986  Nason et al.
4,685,903 A  8/1987  Cable et al.
(Continued)

FOREIGN PATENT DOCUMENTS

CN  114787932 A  7/2022
EP   8567594 A1  11/2019
(Continued)

OTHER PUBLICATIONS

Güemes, Amparo, et al. "Predicting quality of overnight glycaemic control in type 1 diabetes using binary classifiers." IEEE Journal of Biomedical and Health Informatics 24.5 (2019): 1439-1446. (Year: 2019).*

(Continued)

*Primary Examiner* — Jason B Dunham
*Assistant Examiner* — Constantine Siozopoulos
(74) *Attorney, Agent, or Firm* — Weaver Austin Villeneuve Sampson LLP

(57) ABSTRACT

Technologies are provided for classifying detected events as labeled event combinations. Input data for different combinations of detected events are received at a server system, and each combination of detected events is processed at the server system. Processing can include classifying that combination of detected events at a classifier to map that combination of detected events to a probability of an increased insulin delivery demand or a probability of a decreased insulin delivery demand, and labeling each classified combination of detected events with a label to generate a corresponding labeled event combination that has the probability of the increased insulin delivery demand or the probability of the decreased insulin delivery demand. Each labeled event combination can be stored in storage as a database of labeled event combinations, and selected ones of (Continued)

the labeled event combinations can be processed at a client application to generate an output result.

20 Claims, 18 Drawing Sheets

(51) Int. Cl.
| | |
|---|---|
| *G16H 50/50* | (2018.01) |
| *G16H 40/67* | (2018.01) |
| *G16H 10/40* | (2018.01) |
| *G16H 20/60* | (2018.01) |
| *G06F 16/23* | (2019.01) |
| *G06F 16/245* | (2019.01) |
| *A61B 5/11* | (2006.01) |
| *A61B 5/145* | (2006.01) |
| *A61B 5/00* | (2006.01) |
| *A61M 5/172* | (2006.01) |
| *G16H 20/30* | (2018.01) |
| *G06F 18/214* | (2023.01) |
| *G06N 7/01* | (2023.01) |
| *G06V 10/80* | (2022.01) |
| *G06V 40/20* | (2022.01) |

(52) U.S. Cl.
CPC .......... *A61B 5/4866* (2013.01); *A61B 5/7267* (2013.01); *A61B 5/7278* (2013.01); *A61B 5/7282* (2013.01); *A61M 5/1723* (2013.01); *G06F 16/2379* (2019.01); *G06F 16/245* (2019.01); *G06F 18/214* (2023.01); *G06F 18/2148* (2023.01); *G06N 7/01* (2023.01); *G06V 10/809* (2022.01); *G16H 10/40* (2018.01); *G16H 20/17* (2018.01); *G16H 20/30* (2018.01); *G16H 20/60* (2018.01); *G16H 40/67* (2018.01); *G16H 50/50* (2018.01); *G06V 40/20* (2022.01)

(56) References Cited

U.S. PATENT DOCUMENTS

| | | | |
|---|---|---|---|
| 4,755,173 | A | 7/1988 | Konopka et al. |
| 5,080,653 | A | 1/1992 | Voss et al. |
| 5,097,122 | A | 3/1992 | Colman et al. |
| 5,391,250 | A | 2/1995 | Cheney, II et al. |
| 5,485,408 | A | 1/1996 | Blomquist |
| 5,505,709 | A | 4/1996 | Funderburk et al. |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,485,465 | B2 | 11/2002 | Moberg et al. |
| 6,544,212 | B2 | 4/2003 | Galley et al. |
| 6,554,798 | B1 | 4/2003 | Mann et al. |
| 6,558,320 | B1 | 5/2003 | Causey, III et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,659,980 | B2 | 12/2003 | Moberg et al. |
| 6,736,797 | B1 | 5/2004 | Arsen et al. |
| 6,749,587 | B2 | 6/2004 | Flaherty |
| 6,752,787 | B1 | 6/2004 | Causey, III et al. |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 6,817,990 | B2 | 11/2004 | Yap et al. |
| 6,932,584 | B2 | 8/2005 | Gray et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,621,893 | B2 | 11/2009 | Moberg et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,019,410 | B1 | 9/2011 | Bharmi et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 9,037,254 | B2 | 5/2015 | John |
| 9,622,675 | B2 | 4/2017 | Leyde et al. |
| 10,102,342 | B1 | 10/2018 | Vleugels et al. |
| 10,342,923 | B2 | 7/2019 | Henrich et al. |
| 10,532,211 | B2 | 1/2020 | Ghaffari et al. |
| 10,593,231 | B2 | 3/2020 | Cahan et al. |
| 10,716,896 | B2 | 7/2020 | O'Connor et al. |
| 11,024,142 | B2 | 6/2021 | Tunnell et al. |
| 11,367,517 | B2 | 6/2022 | Vleugels |
| 2007/0123819 | A1 | 5/2007 | Mernoe et al. |
| 2009/0062730 | A1 | 3/2009 | Woo |
| 2009/0069787 | A1 | 3/2009 | Estes et al. |
| 2010/0160861 | A1 | 6/2010 | Causey, III et al. |
| 2012/0266251 | A1 | 10/2012 | Birtwhistle et al. |
| 2013/0046281 | A1 | 2/2013 | Javitt |
| 2015/0134356 | A1 | 5/2015 | Atlas et al. |
| 2016/0184518 | A1 | 6/2016 | Freeman et al. |
| 2016/0270717 | A1 | 9/2016 | Luna et al. |
| 2016/0317077 | A1 | 11/2016 | Sillay |

(56) References Cited

U.S. PATENT DOCUMENTS

| | | |
|---|---|---|
| 2017/0049383 A1 | 2/2017 | McMahon |
| 2017/0053552 A1 | 2/2017 | Zhong et al. |
| 2017/0164878 A1 | 6/2017 | Connor |
| 2017/0188979 A1 | 7/2017 | Volpe |
| 2017/0203039 A1 | 7/2017 | Desborough et al. |
| 2017/0220772 A1 | 8/2017 | Vleugels et al. |
| 2017/0258986 A1 | 9/2017 | Tsoukalis |
| 2018/0169334 A1 | 6/2018 | Grosman |
| 2018/0174675 A1 | 6/2018 | Roy et al. |
| 2018/0178061 A1 | 6/2018 | O'Larte et al. |
| 2018/0318529 A1 | 11/2018 | Davidson et al. |
| 2018/0353682 A1 | 12/2018 | Laurence et al. |
| 2019/0251456 A1 | 8/2019 | Constantin et al. |
| 2019/0307958 A1 | 10/2019 | Yang |
| 2019/0365286 A1 | 12/2019 | Powers, III et al. |
| 2020/0015739 A1 | 1/2020 | Abraham et al. |
| 2020/0135320 A1 | 4/2020 | Vleugels |
| 2020/0286612 A1 | 9/2020 | Mears |
| 2020/0289373 A1 | 9/2020 | Vleugels |
| 2020/0294645 A1 | 9/2020 | Vleugels |
| 2020/0375549 A1* | 12/2020 | Wexler ............... G16H 50/20 |
| 2021/0060248 A1 | 3/2021 | Golenberg et al. |
| 2021/0060249 A1 | 3/2021 | Golenberg et al. |
| 2021/0090727 A1 | 3/2021 | Rosinko et al. |
| 2021/0100951 A1 | 4/2021 | Chase |
| 2021/0177345 A1 | 6/2021 | Wu et al. |
| 2021/0178064 A1 | 6/2021 | Vleugels et al. |
| 2021/0178066 A1 | 6/2021 | Monirabbasi |
| 2021/0178069 A1 | 6/2021 | Grosman et al. |
| 2021/0183491 A1 | 6/2021 | Grosman et al. |
| 2021/0183522 A1 | 6/2021 | Lintereur et al. |
| 2022/0062553 A1 | 3/2022 | Constantin et al. |
| 2023/0005586 A1* | 1/2023 | Eghtesadi ............ G16H 50/20 |
| 2023/0158235 A1 | 5/2023 | Golenberg et al. |

FOREIGN PATENT DOCUMENTS

| | | | |
|---|---|---|---|
| EP | 4073811 A1 | 10/2022 | |
| WO | 2020072128 A1 | 4/2020 | |
| WO | WO-2020252496 A1 * | 12/2020 | ............ G06N 20/00 |
| WO | 2021119549 A1 | 6/2021 | |

OTHER PUBLICATIONS

International Search Report and Written Opinion dated Mar. 25, 2021, in Application No. PCT/US2020/064703.

U.S. Non-Final office Action dated Nov. 15, 2022 in U.S. Appl. No. 17/118,957.

U.S. Non-Final Office Action dated Nov. 16, 2022, in U.S. Appl. No. 17/120,055.

International Preliminary Report on Patentability dated May 17, 2022 in corresponding international application PCT/US2020/064703 (7 pages).

Extended European Search Report dated May 4, 2023 in Application No. EP23154072.5.

Carroll, L., "Experimental Phone App Works With Insulin Pumps To Control Diabetes", Reuters, Healthcare & Pharma, Jan. 29, 2019, 8 pages. available at https://www.reuters.com/article/us-health-diabetes-apps/experimental-phoneapp-works-with-insulin-pumps-to-control-diabetes-idUSKCN1PN32D.

Smith, A., "FDA Approves New Smart Insulin Pump", Oct. 3, 2016, 3 pages.

U.S. Final Office Action dated Feb. 28, 2023 in U.S. Appl. No. 17/118,957.

U.S. Non-Final office Action dated Jan. 24, 2023 in U.S. Appl. No. 17/005,939.

U.S. Non-Final Office Action dated Jul. 20, 2023, in U.S. Appl. No. 16/514,748.

* cited by examiner

| ADJUSTABLE PARAMETERS (CONSTANTS AND COEFFICIENTS) (UNITS): DESCRIPTION | DETECTED EVENT | | | | |
|---|---|---|---|---|---|
| | PHYSICAL ACTIVITY | MEAL INGESTION | SLEEP | SICKNESS (MAYBE RELATED TO HEART RATE WITH BODY TEMPERATURE) | STRESS (MAYBE RELATED TO HEART RATE WITH BODY TEMPERATURE) |
| FIRST PATIENT-SPECIFIC TIME CONSTANT ( ): (MINUTE): THE NET INSULIN DIFFUSION RATE BETWEEN THE SUBCUTANEOUS COMPARTMENT AND THE PLASMA COMPARTMENT | X | N/A | X | | |
| SECOND PATIENT-SPECIFIC TIME CONSTANT ( ): (MINUTE): THE RATE OF INSULIN REMOVAL | X | N/A | X | X | X |
| THIRD PATIENT-SPECIFIC TIME CONSTANT ( ): (MINUTE): THE NET GLUCOSE DIFFUSION RATE BETWEEN THE SUBCUTANEOUS COMPARTMENTS AND THE PLASMA COMPARTMENT | X | N/A | X | X | X |
| FOURTH PATIENT-SPECIFIC TIME CONSTANT ( ): (MINUTE): RATE OF GLUCOSE REMOVAL | X | N/A | N/A | X | X |
| FIFTH PATIENT-SPECIFIC TIME CONSTANT ( ): (MINUTE): NET GLUCOSE DIFFUSION RATE BETWEEN THE DIGESTION COMPARTMENTS AND THE PLASMA COMPARTMENT | X | X | N/A | X | X |
| PATIENT-SPECIFIC MEAL ABSORPTION CONSTANT ($K_M$) (MG/CARB): REPRESENTS A STOCHIOMETRIC CONVERSION OF THE CARBOHYDRATES (CARB) FROM MEAL INGESTION INTO GLUCOSE CONCENTRATION | X | X | N/A | X | X |
| INSULIN UTILIZATION OF GLUCOSE PARAMETER ($K_I$): MG/(U MINUTE) | X | N/A | X | X | X |

TABLE 1 - EXAMPLES OF DETECTED EVENTS AND ADJUSTABLE PARAMETERS THAT MAY BE IMPACTED AND MODIFIED IN RESPONSE TO THAT DETECTED EVENT

FIG. 14

METHOD AND SYSTEM FOR CLASSIFYING DETECTED EVENTS AS LABELED EVENT COMBINATIONS FOR PROCESSING AT A CLIENT APPLICATION

CROSS-REFERENCE TO RELATED APPLICATION

This application claims the benefit of U.S. provisional patent application No. 62/948,007 filed Dec. 13, 2019.

TECHNICAL FIELD

The present technology is generally related to insulin therapy, and more particularly to a method and system for classifying detected events as labeled event combinations for processing at a client application.

BACKGROUND

Medical therapy delivery systems, such as fluid infusion devices, are relatively well known in the medical arts for use in delivering or dispensing an agent, such as insulin or another prescribed medication, to a patient. A typical medication infusion device includes a fluid pump mechanism and an associated drive system that actuates a plunger or piston of a fluid reservoir to deliver fluid medication from the reservoir to the body of a patient via a fluid delivery conduit between the reservoir and the body of a patient. Use of infusion pump therapy has been increasing, especially for delivering insulin to diabetic patients.

BRIEF SUMMARY

A method, system and non-transient computer-readable medium are provided for classifying detected events as labeled event combinations for processing at a client application. Input data for different combinations of detected events are received at a server system, and each combination of detected events is processed at the server system. Processing can include classifying that combination of detected events at a classifier to map that combination of detected events to a probability of an increased insulin delivery demand or a probability of a decreased insulin delivery demand, and labeling each classified combination of detected events with a label to generate a corresponding labeled event combination that has the probability of the increased insulin delivery demand or the probability of the decreased insulin delivery demand. Each labeled event combination can be stored in storage as a database of labeled event combinations, and selected ones of the labeled event combinations can be processed at the client application to generate an output result.

Each labeled event combination can be correlated to: a decreased insulin delivery demand when the probability of the decreased insulin delivery demand is greater than a first threshold; an increased insulin delivery demand when the probability of the increased insulin delivery demand is greater than a second threshold; or an ordinary insulin delivery demand when the probability of the decreased insulin delivery demand is less than the first threshold and the probability of the increased insulin delivery demand is less than the second threshold.

In some aspects, at least some of the events can be detected using a gesture detection device. At least some of the events can include, for example, therapy-related data and settings from an insulin infusion device of a user; meal data comprising predicted carbohydrate intake data for the user; and a specific physical activity performed by the user. The specific activities that are indicative of the physical behavior of the user can include things such as a meal ingestion event; a sleep event; a physical activity event; an exercise event and a work-related event.

In one embodiment, the client application can be a controller for an insulin infusion device, and selected ones of the labeled event combinations can be processed at the controller to generate one or more therapy parameters for controlling delivery of insulin via the insulin infusion device. The controller can generate, based on the one or more therapy parameters, recommended settings or commands to control delivery of insulin via the insulin infusion device.

In another embodiment, the client application can be a mathematical model that represents physiology of a user. The mathematical model can be trained based on the selected ones of the labeled event combinations to generate an adapted mathematical model that simulates a physiological blood glucose response of the user in response to the labeled event combinations.

In another embodiment, the client application can be a healthcare management application for insulin therapy management. Events associated with the user that are indicative of physical behavior of the user and correspond to the selected ones of the labeled event combinations can be tracked and one or more user interfaces can be generated that provide information indicating an impact of the tracked events on blood glucose levels of the user and insulin demand of the user.

In another embodiment, the client application can be an application for calibrating an insulin therapy system of the user. Selected ones of the labeled event combinations can be processed at the application for calibrating the insulin therapy system of the user to generate recommended therapy settings and parameters for calibrating the insulin therapy system of the user.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 14 is a table that shows examples of adjustable therapy parameters and whether they are impacted by a detected event or not impacted by the detected event in accordance with certain embodiments;

DETAILED DESCRIPTION

Figure 1:
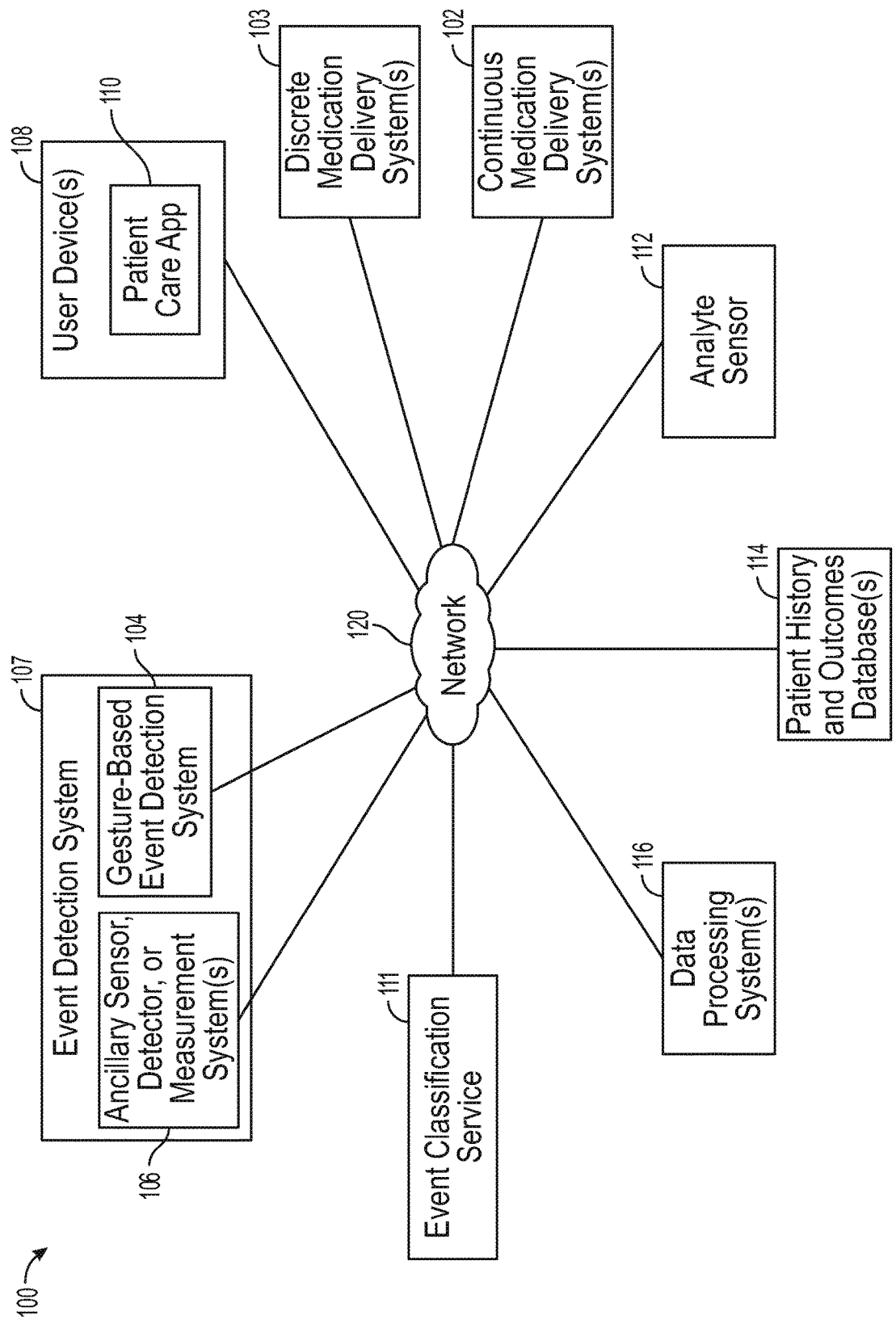
FIG. 1 is a simplified block diagram representation of an exemplary embodiment of a system that includes a medication delivery system that responds to changes in patient activity as indicated by the output of a gesture-based event detection system.

Control schemes have been developed to allow insulin infusion devices to monitor and regulate a patient's blood glucose level in a substantially continuous and autonomous manner. An insulin infusion device can be operated in an automatic mode wherein basal insulin is delivered at a rate that is automatically adjusted for the user. Moreover, an insulin infusion device can be operated to automatically calculate, recommend, and deliver insulin boluses as needed (e.g., to compensate for meals consumed by the user). Ideally, the amount of an insulin bolus should be accurately calculated and administered to maintain the user's blood glucose within the desired range. In particular, an automatically generated and delivered insulin bolus should safely manage the user's blood glucose level and keep it above a defined threshold level. To this end, an insulin infusion device operating in an automatic mode uses continuous glucose sensor data and control algorithms to regulate the user's blood glucose, based on a target glucose setpoint setting and user-initiated meal announcements that typically include estimations of the amount of carbohydrates to be consumed in an upcoming meal.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

It should be understood that various aspects disclosed herein may be combined in different arrangements than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Program code instructions may be configurable to be executed by one or more processors, such as one or more digital signal processors (DSPs), general purpose microprocessors, controllers, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

FIG. 1 is a simplified block diagram representation of an exemplary embodiment of a system 100 that responds to changes in the user's activity (e.g., eating, sleeping, exercise, and/or working habits) by regulating operation of a continuous medication delivery system 102 and/or a discrete medication delivery system 103 in an appropriate manner. In certain embodiments, the continuous medication delivery system 102 and/or the discrete medication delivery system 103 responds to changes in patient activity as indicated by the output of a gesture-based event detection system 104 and/or the output of at least one ancillary sensor, detector, or measurement system 106 (hereinafter referred to as ancillary system(s) 106). Certain embodiments of the system 100 include, without limitation: the continuous medication delivery system 102 that delivers medication to a user; the discrete medication delivery system 103 (or device) that delivers medication to a user; an event detection system 107 that includes at least one gesture-based event detection system 104 that monitors user behavior and/or status to obtain gesture data that indicates user activity events or behavior and at least one ancillary system 106; at least one user device 108 that includes or cooperates with a suitably written and configured patient care application 110; an event classification service or application 111; an analyte sensor 112 to measure a physiological characteristic of the user, such that sensor data obtained from the analyte sensor 112 can be used to control, regulate, configure or otherwise influence the operation of the continuous medication delivery system 102 and/or the discrete insulin therapy system 103; and at least one patient history and outcomes database 114. In accordance with certain cloud-implemented embodiments, the system includes at least one data processing system 116, which may be in communication with any or all of the other components of the system 100. In some examples, the discrete medication delivery system 103 includes one or more user device(s) 108. Other configurations and topologies for the system 100 are also contemplated here, such as a system that includes additional intermediary, interface, or data repeating devices in the data path between a sending device and a receiving device.

As will be described in greater detail below, the event classification service (or app) 111 is provided for classifying detected events as labeled events and for classifying combinations of detected events as labeled event combinations. Depending on the embodiment, the event classification service 111 may be distributed across one or more different devices 102, 103, 104, 106, 108, 112, 114, 116 in the system 100 and the subject matter described herein is not limited to any particular implementation. Various embodiments of the event classification service 111 will be described in greater detail below with reference to FIGS. 9 through 16.

At least some of the components of the system 100 are communicatively coupled with one another to support data communication, signaling, and/or transmission of control commands as needed, via at least one communications network 120. The at least one communications network 120 may support wireless data communication and/or data communication using tangible data communication links. FIG. 1 depicts network communication links in a simplified manner. In practice, the system 100 may cooperate with and leverage any number of wireless and any number of wired data communication networks maintained or operated by various entities and providers. Accordingly, communication between the various components of the system 100 may involve multiple network links and different data communication protocols. In this regard, the network can include or cooperate with any of the following, without limitation: a local area network; a wide area network; the Internet; a personal area network; a near-field data communication link; a cellular communication network; a satellite communication network; a video services or television broadcasting network; a network onboard a vehicle; or the like. The components of the system 100 may be suitably configured to support a variety of wireless and wired data communication protocols, technologies, and techniques as needed for compatibility with the at least one communication network 120.

The system 100 can support any type of continuous medication delivery system 102 and discrete medication delivery system 103 that is compatible with the features and functionality described here. The continuous medication delivery system 102 may be implemented as an electronic device that is operated to regulate the delivery of medication fluid to the user. In certain embodiments, the continuous medication delivery system 102 includes or is realized as an insulin infusion device, e.g., a portable patient-worn or patient-carried insulin pump or the like. In this case, the medication delivery system 102 is "continuous" in that it continuously measures a user's blood glucose levels and delivers insulin (or other medication) to the user. The discrete medication delivery system 103 may be realized as a user-activated or user-actuated fluid delivery device, such as a manual syringe, an injection pen, a smart insulin pen, or the like. In this case, the medication delivery system 103 is "discrete" in that it discretely delivers insulin (or other medication) to the user.

Both the continuous medication delivery system 102 and the discrete medication delivery system 103 can be utilized in conjunction with one or more analyte sensors. In such embodiments, the analyte sensor 112 includes or is realized as a glucose meter, a glucose sensor, or a continuous glucose monitor. For the sake of brevity, conventional techniques related to insulin infusion device operation, infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Generally, a fluid infusion device (such as an insulin infusion device) includes a fluid pump mechanism having a motor or other actuation arrangement that is operable to linearly displace a plunger (or stopper) of a fluid reservoir provided within the fluid infusion device to deliver a dosage of fluid medication, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For a glucose control system suitable for use by diabetic patients, a closed-loop or automatic operating mode can be used to generate insulin dosage commands based on a difference between a current (or most recent) measurement of the interstitial fluid glucose level in the body of the user and a target (or reference) glucose setpoint value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Figure 2:
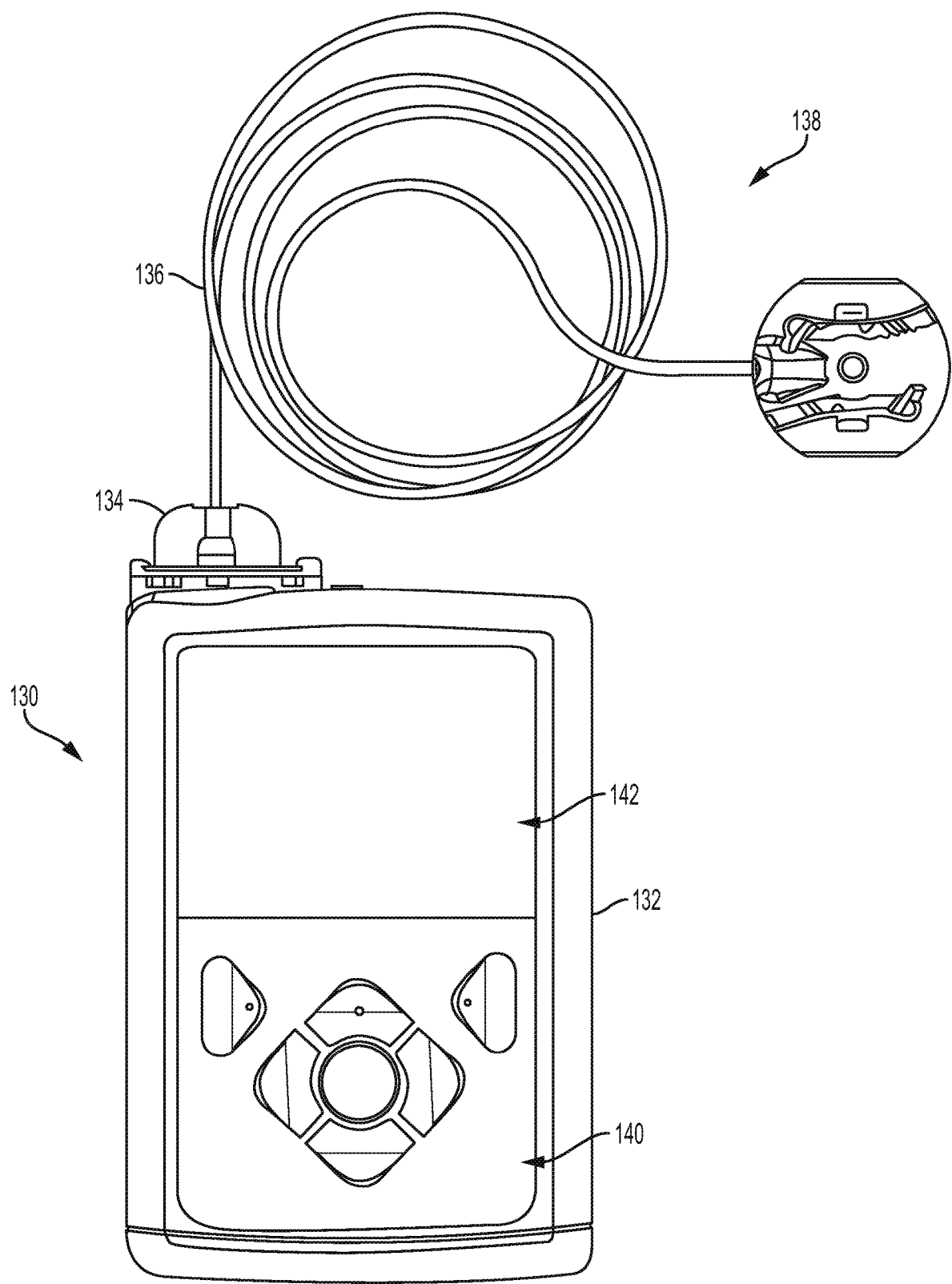
FIG. 2 is a plan view of an exemplary embodiment of an insulin infusion device that is suitable for use as the medication delivery system shown in FIG. 1.

FIG. 2 is a plan view of an exemplary embodiment of an insulin infusion device 130 suitable for use as the medication delivery system 102 shown in FIG. 1. The insulin infusion device 130 is a portable medical device designed to be carried or worn by the patient. The insulin infusion device 130 is one example of a device that can be used as part of the continuous medication delivery system 102 of FIG. 1. The insulin infusion device 130 can deliver insulin to a user without the need for manual injections. The insulin infusion device 130 can be part of a continuous insulin therapy system that includes one or more sensors such as a continuous glucose monitor. The insulin infusion device 130 can provide fast-acting insulin through a small tube placed under the skin, delivering two types of doses: basal or "background" insulin, which can be delivered continuously in tiny doses throughout the day and night; and bolus insulin to cover an increase in blood glucose from meals and/or to correct high blood glucose levels. The insulin infusion device 130 can provide insulin based on preprogrammed basal and bolus settings.

The illustrated embodiment of the insulin infusion device 130 includes a housing 132 adapted to receive an insulin-containing reservoir (hidden from view in FIG. 2). An opening in the housing 132 accommodates a fitting 134 (or cap) for the reservoir, with the fitting 134 being configured to mate or otherwise interface with tubing 136 of an infusion set 138 that provides a fluid path to/from the body of the user. In this manner, fluid communication from the interior of the insulin reservoir to the user is established via the tubing 136. The illustrated version of the insulin infusion device 130 includes a human-machine interface (HMI) 140 (or user interface) that includes elements that can be manipulated by the user to administer a bolus of fluid (e.g., insulin), to change therapy settings, to change user preferences, to select display features, and the like. The insulin infusion device 130 also includes a display 142, such as a liquid crystal display (LCD) or another suitable display technology, that can be used to present various types of information or data to the user, such as, without limitation: the current glucose level of the patient; the time; a graph or chart of the patient's glucose level versus time; device status indicators; etc. The insulin infusion device 130 may be configured and controlled to support other features and interactive functions described in more detail below.

Figure 3A:
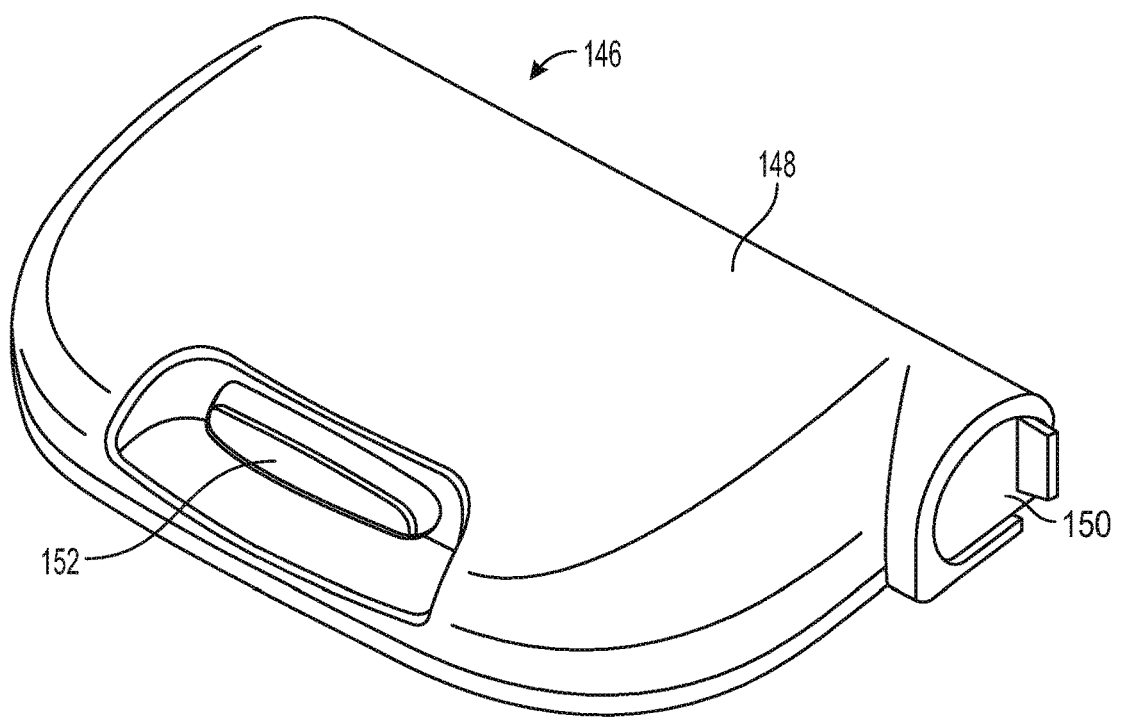
FIG. 3A is a top perspective view of an embodiment of an insulin infusion device implemented as a patch pump device that is suitable for use as the medication delivery system shown in FIG. 1.

FIG. 3A is a top perspective view of an embodiment of an insulin infusion device 146 implemented as a patch pump device that is suitable for use as the medication delivery system 102 shown in FIG. 1. The insulin infusion device 146 can be implemented as a combination device that includes an insertable insulin delivery cannula and an insertable glucose sensor (both of which are hidden from view in FIG. 3A). In such an implementation, the glucose sensor may take the place of the separate analyte sensor 112 shown in FIG. 1. The insulin infusion device 146 is another example of a device that can be used to implement the continuous medication delivery system 102 of FIG. 1. In this embodiment, the insulin infusion device 146 includes a housing 148 that serves as a shell for a variety of internal components. FIG. 3A shows the insulin infusion device 146 with a removable fluid cartridge 150 installed and secured therein. The housing 148 is suitably configured to receive, secure, and release the removable fluid cartridge 150. The insulin infusion device 146 includes at least one user interface feature, which can be actuated by the patient as needed. The illustrated embodiment of the insulin infusion device 146 includes a button 152 that is physically actuated. The button 152 can be a multipurpose user interface if so desired to make it easier for the user to operate the insulin infusion device 146. In this regard, the button 152 can be used in connection with one or more of the following functions, without limitation: waking up the processor and/or electronics of the insulin infusion device 146; triggering an insertion mechanism to insert a fluid delivery cannula and/or an analyte sensor into the subcutaneous space or similar region of the user; configuring one or more settings of the insulin infusion device 146; initiating delivery of medication fluid from the fluid cartridge 150; initiating a fluid priming operation; disabling alerts or alarms generated by the insulin infusion device 146; and the like. In lieu of the button 152, the insulin infusion device 146 can employ a slider mechanism, a pin, a lever, a switch, a touch-sensitive element, or the like. In certain embodiments, the insulin infusion device 146 may be configured and controlled to support other features and interactive functions described in more detail below.

Figure 3B:
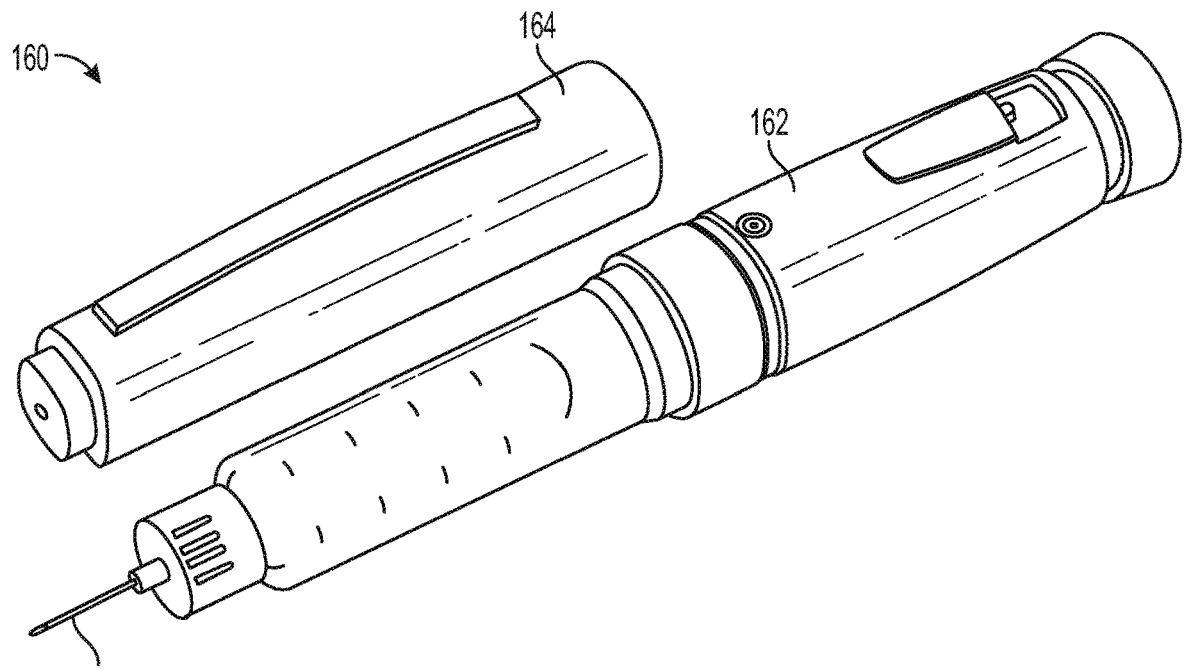
FIG. 3B is a perspective view of an exemplary embodiment of a smart insulin pen that is suitable for use as the medication delivery system shown in FIG. 1.

FIG. 3B is a perspective view of an exemplary embodiment of a smart insulin pen 160 suitable for use as the medication delivery system shown in FIG. 1. The smart insulin pen 160 is one example of a device that can be used as part of the discrete medication delivery system 103 of FIG. 1. The pen 160 includes an injector body 162 and a cap 164. FIG. 3B shows the cap 164 removed from the injector body 162, such that a delivery needle 166 is exposed. The pen 160 includes suitably configured electronics and processing capability to communicate with an application running on a user device, such as a smartphone, to support various functions and features such as: tracking active insulin; calculating insulin dosages (boluses); tracking insulin dosages; monitoring insulin supply levels; patient reminders and notifications; and patient status reporting. In certain embodiments, the smart insulin pen 160 can receive insulin dosage recommendations or instructions and/or recommended dosing times (or a recommended dosing schedule). Moreover, the smart insulin pen 160 may be configured and controlled to support other features and interactive functions described in more detail below.

Figure 4:
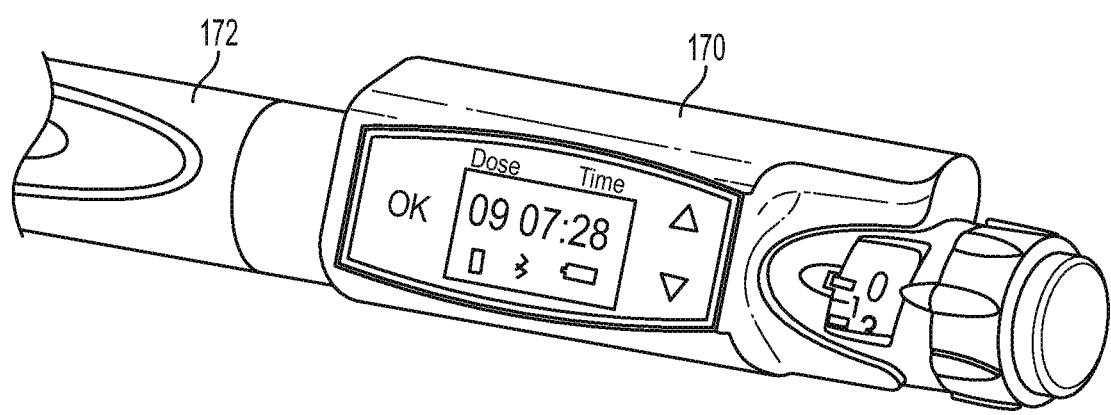
FIG. 4 is a perspective view of an exemplary embodiment of a smart pen accessory that is suitable for use with the medication delivery system shown in FIG. 1.

FIG. 4 is a perspective view of an exemplary embodiment of a smart pen accessory 170 that is suitable for use with the medication delivery system 102 shown in FIG. 1. The smart pen accessory 170 is one example of a device that can be used as part of the discrete medication delivery system 103 of FIG. 1. In particular, the smart pen accessory 170 cooperates with a "non-smart" insulin pen that lacks the intelligence and functionality of a smart insulin pen (as described). The smart pen accessory 170 can be realized as a pen cap, a clip-on apparatus, a sleeve, or the like. The smart pen accessory 170 is attached to an insulin pen 172 such that the smart pen accessory 170 can measure the amount of insulin delivered by the insulin pen 172. The insulin dosage data is stored by the smart pen accessory 170 along with corresponding date/time stamp information. In certain embodiments, the smart pen accessory 170 can receive, store, and process additional patient-related or therapy-related data, such as glucose data. Indeed, the smart pen accessory 170 may also support various features and functions described in the context of the smart insulin pen 160. For example, the smart pen accessory 170 may be configured to receive insulin dosage recommendations or instructions and/or recommended dosing times (or a recommended dosing schedule). Moreover, the smart pen accessory 170 may be configured and controlled to support other features and interactive functions described in more detail below.

Figure 5:
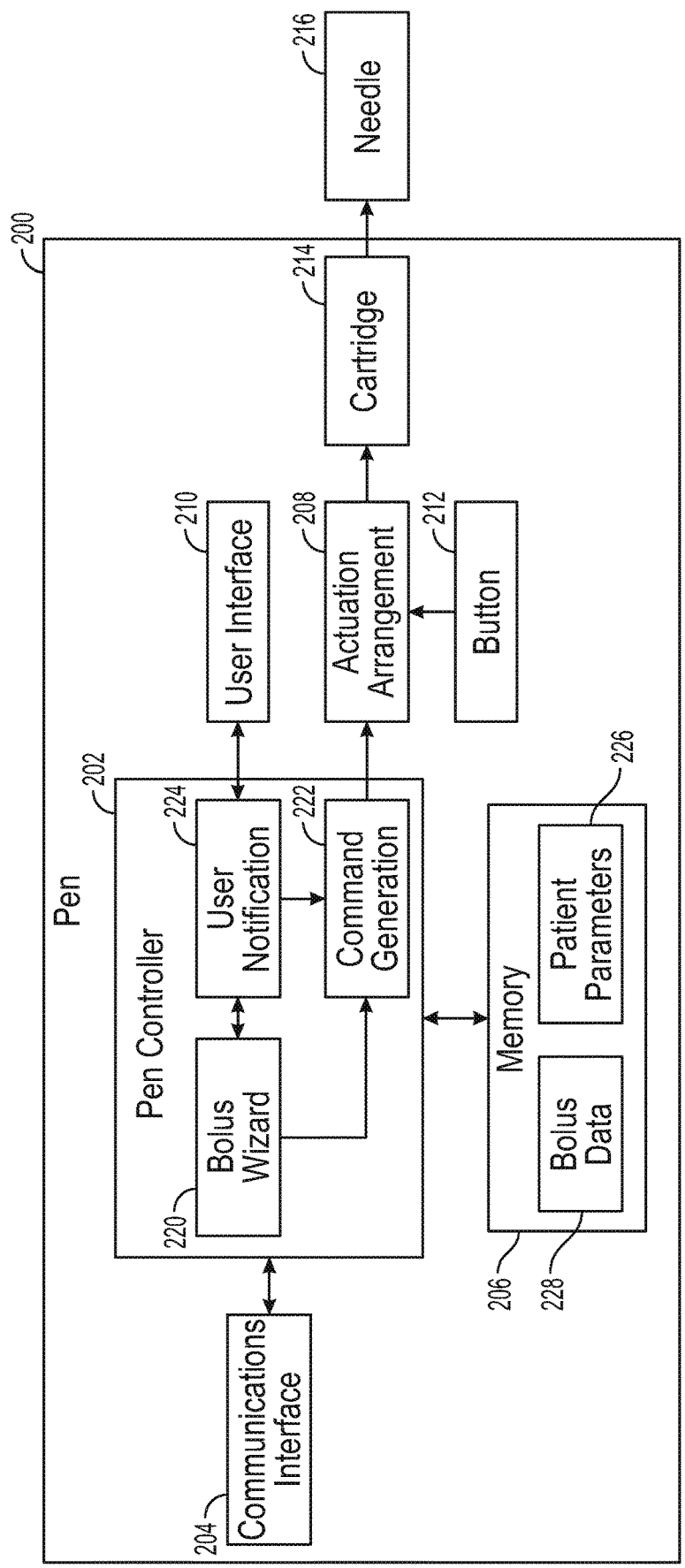
FIG. 5 is a block diagram of an exemplary embodiment of an injection pen suitable for use in the injection system of FIG. 1.

FIG. 5 depicts an exemplary embodiment of an injection pen 200 suitable for use as the discrete medication delivery system 103 of FIG. 1 in accordance with one or more embodiments. The injection pen 200 is one example of a device that can be used as part of the discrete medication delivery system 103 of FIG. 1. The illustrated injection pen 200 includes, without limitation, a pen controller 202, a communications interface 204, a data storage element (or memory) 206, an actuation arrangement 208, and user interface elements 210, 212. The pen controller 202 is coupled to the communications interface 204, the memory 206, the actuation arrangement 208, and the user interface elements 210, 212, and the pen controller 202 is suitably configured to support the operations, tasks, and/or processes described herein. In this regard, the pen controller 202 supports operation of the actuation arrangement 208 in response to manual actuation of a user interface element 212 to deliver a particular bolus amount of fluid from a fluid container 214 (e.g., a cartridge or reservoir) to an injection site in the body 104 of a patient via a needle 216.

The communications interface 204 generally represents the hardware, circuitry, logic, firmware and/or other components of the injection pen 200 that are coupled to the pen controller 202 and configured to support communications between the injection pen 200 and one or more external electronic devices of an injection system 100 (e.g., the blood glucose meter 106, the glucose sensing arrangement 108, and/or the electronic device 110). In exemplary embodiments, the communications interface 204 includes or is otherwise coupled to one or more transceiver units capable of supporting wireless communications; however, in some embodiments, the communications interface 204 may be configured to support wired communications.

The user interface element(s) 210 generally represents the hardware, circuitry, logic, firmware and/or other components of the injection pen 200 configured to support user interactions between the pen controller 202 and a patient or user. The one or more user interface element(s) 210 associated with the injection pen 200 may include at least one input user interface element, such as, for example, a button, a keypad, a knob, a touch panel, a touchscreen, and/or the like. Additionally, the one or more user interface element(s) 210 may include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. In the illustrated embodiment, user interface element 212 represents an input user interface element of the injection pen 200 that is actuatable by a user to produce corresponding operation of the actuation arrangement 208 to deliver a bolus of fluid from the fluid container 214 via the needle 216. In one or more embodiments, the input user interface element 212 is realized as a tactile depressible button that is associated with the delivery of a bolus from the injection pen 200, and accordingly, the input user interface element 212 may alternatively be referred to herein, without limitation, as a delivery button.

The pen controller 202 generally represents the hardware, circuitry, logic, firmware and/or other component(s) of the injection pen 200 that is configured to determine bolus dosage commands for configuring or otherwise operating the actuation arrangement 208 to deliver fluid from the fluid container 214 and perform various additional tasks, operations, functions and/or operations described herein. Depending on the embodiment, the pen controller 202 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software instructions executed by the pen controller 202, or in any practical combination thereof.

In exemplary embodiments, the pen controller 202 includes or otherwise accesses the data storage element or memory 206, which may be realized using any sort of non-transitory computer-readable medium capable of storing programming instructions for execution by the pen controller 202. The computer-executable programming instructions, when read and executed by the pen controller 202, cause the pen controller 202 to perform the tasks, operations, functions, and processes described herein. In this regard, a control scheme or algorithm implemented by the pen controller 202 may be realized as control application code that is stored or otherwise maintained in the memory 206 and executed by the pen controller 202 to implement or otherwise provide one or more of the components in software. For example, the control application code may be executed by the controller 202 to generate a bolus wizard application 220 that calculates or otherwise determines the amount of fluid to be bolused to a patient. Similarly, the pen controller 202 may also implement or otherwise execute a command generation application 222 that converts a bolus amount from the bolus wizard application 220 into a corresponding command for operating or otherwise configuring the actuation arrangement 208 for dispensing the bolus amount from the container 214. The illustrated pen controller 202 also implements or otherwise executes a user notification application 224 that supports interactions with the patient or other users via the user interface element(s) 210 associated with the injection pen 200, as described in greater detail below.

Still referring to FIG. 5, the parameter registers 226 generally represent the hardware, circuitry and/or other components of the injection pen 200 that are configured to store the patient-specific physiological parameters or other control information utilized by the bolus wizard application 220 of the pen controller 202 in determining a bolus amount in a patient-specific manner. For example, the parameter registers 226 may store or otherwise maintain one or more patient-specific insulin sensitivity factor values, carbohydrate-to-insulin ratio values, insulin action speed values, target glucose values, and the like. The patient-specific insulin sensitivity factor value reflects the patient's sensitivity to insulin (e.g., an amount of drop in glucose level per unit of insulin administered). In practice, multiple different patient-specific insulin sensitivity factor values may be input by a user and stored by the injection pen 200 in association with particular time periods to support subdividing the day into multiple segments that reflect or otherwise account for diurnal variations in the patient's insulin sensitivity. The carbohydrate-to-insulin ratio value defines how many grams of carbohydrates one unit of insulin can compensate for, and similarly, multiple different carbohydrate-to-insulin ratio values may be input by a user and stored by the injection pen 200 in association with particular time periods to account for diurnal variations exhibited by the patient. The insulin action speed value represents the amount of time insulin remains active in the patient's body (e.g., the amount of time required to clear a unit of insulin).

In exemplary embodiments, the parameter registers 226 are capable of storing or otherwise maintaining a low target glucose value ($T_L$) and a high target glucose value ($T_H$), which are utilized when calculating the bolus amount. In this regard, the high target glucose value ($T_H$) is the desired glucose level that the user would like to achieve or stay below after delivering a bolus, and the low target glucose value ($T_L$) is the desired glucose level that the user would like to achieve or stay above after delivering a bolus. Again, multiple different sets of target glucose values may be input by a user and stored by the injection pen 200 in association with particular time periods to support subdividing the day into multiple segments.

In exemplary embodiments, the memory 206 also includes registers 228 (or other allocation) configured to store historical bolus data for the injection pen 200. In this regard, the bolus data portion 228 of memory 206 stores or otherwise maintains information identifying the respective amounts of previous boluses and the respective delivery times associated with those previous boluses. As described in greater detail below in the context of FIG. 3, the historical bolus data for the injection pen 200 is utilized to calculate, estimate, or otherwise determine the amount of active insulin on-board (IOB) in the body 104 of the patient using the patient-specific insulin action speed value.

In the embodiment of FIG. 5, the actuation arrangement 208 generally represents the hardware, circuitry and/or other electrical, mechanical, or electromechanical components of the injection pen 200 that are configured to enable or otherwise facilitate delivering boluses of fluid from the fluid container 214 to the patient's body 104 via the needle 216. For example, the actuation arrangement 208 may include a motor mechanically coupled to a drive train assembly configured to translate rotational motor motion into linear displacement of a slide, shaft, or the like that produces a corresponding displacement of a plunger or stopper within the fluid container 214 towards the needle 216. In an alternative embodiment, the actuation arrangement 208 includes adjustable or configurable drive train components that are configured to selectively restrict or otherwise limit the range of motion (or amount of displacement) of the plunger or stopper within the fluid container 214, and thereby limit the amount of fluid that may be dispensed from the injection pen 200 when an actuatable user interface element 212 of the injection pen 200 (e.g., a depressible delivery button) is manually manipulated.

It should be understood that FIG. 5 is a simplified representation of the injection pen 200 for purposes of explanation and is not intended to limit the subject matter described herein in any way. In this regard, although FIG. 5 depicts the user interface elements 210, 212 as being integrated with the injection pen 200, in various alternative embodiments, one or more of the user interface element 210, 212 may be integrated with another device in the injection system 100 that is communicatively coupled to the injection pen 200 (e.g., the electronic device 110). Furthermore, although FIG. 5 depicts the fluid container 214 being onboard the injection pen 200, it will be appreciated that the container 214 may be physically separate from the injection pen 200 and detachable, removable or otherwise replaceable upon depletion. Similarly, although FIG. 5 depicts the needle 216 as being separate from the injection pen 200 (e.g., a detachable or replaceable needle), in some embodiments, the needle 216 may be integrated or otherwise fixedly engaged with the housing of the injection pen 200. Additionally, while FIG. 5 depicts registers 226, 228 as being integrated with or into the memory 206, in various embodiments, either or both of the registers 226, 228 may be distinct or otherwise separate from memory 206, and the registers 226, 228 may be integrated with the pen controller 202 or with one another separate from the memory 206.

Referring again to FIG. 1, the analyte sensor 112 may communicate sensor data to the continuous medication delivery system 102 and/or the discrete medication delivery system 103 for use in regulating or controlling operation of the continuous medication delivery system 102 and/or the discrete medication delivery system 103. Alternatively or additionally, the analyte sensor 112 may communicate sensor data to one or more other components in the system 100, such as, without limitation: a user device 108 (for use with the patient care application 110); a data processing system 116; and/or a patient history and outcomes database 114.

The system 100 can support any number of user devices 108 linked to the particular user or patient. In this regard, a user device 108 may be, without limitation: a smartphone device; a laptop, desktop, or tablet computer device; a medical device; a wearable device; a global positioning system (GPS) receiver device; a system, component, or feature onboard a vehicle; a smartwatch device; a television system; a household appliance; a video game device; a media player device; or the like. For the example described here, the continuous medication delivery system 102 and/or the discrete medication delivery system 103 and the at least one user device 108 are owned by, operated by, or otherwise linked to a user/patient. Any given user device 108 can host, run, or otherwise execute the patient care application 110. In certain embodiments, for example, the user device 108 is implemented as a smartphone with the patient care application 110 installed thereon. In accordance with another example, the patient care application 110 is implemented in the form of a website or webpage, e.g., a website of a healthcare provider, a website of the manufacturer, supplier, or retailer of the continuous medication delivery system 102 and/or the discrete medication delivery system 103, or a web site of the manufacturer, supplier, or retailer of the analyte sensor 112. In accordance with another example, the continuous medication delivery system 102 and/or the discrete medication delivery system 103 executes the patient care application 110 as a native function.

In certain embodiments, at least some of the features or output of the gesture-based event detection system 104 and/or the ancillary system(s) 106 can be used to influence features, functions, and/or therapy-related operations of the continuous medication delivery system 102 and/or the discrete medication delivery system 103. In particular, the systems 104, 106 may be suitably configured and operated to generate and provide output (e.g., data, control signals, markers, or flags) that indicates whether the user's behavior or activity is out of the ordinary, unusual, or has significantly changed relative to a currently implemented or active therapy behavior pattern of the user, such that the continuous medication delivery system 102 can dynamically respond in an appropriate manner that contemplates a change in user activity. Likewise, the systems 104, 106 may be suitably configured and operated to generate and provide output (e.g., data, control signals, markers, or flags) to the discrete medication delivery system 103 so that the user can take actions to adjust therapy As described in more detail below, the gesture-based event detection system 104 includes one or more sensors, detectors, measurement devices, and/or readers to automatically detect certain user gestures that correlate to user behavior, eating habits, work habits, or the like (e.g., work-related physical activity, commuting, eating at common meal times, sleeping, exercising, or watching television). The gesture-based event detection system 104 may communicate gesture data to the continuous medication delivery system 102 and/or the discrete medication delivery system 103, the user device 108, and/or the data processing system 116 for processing in an appropriate manner for use in regulating or controlling certain functions of the continuous medication delivery system 102 and/or the discrete medication delivery system 103. For example, the gesture data may be communicated to a user device 108, such that the user device 108 can process the gesture data and inform the user or the continuous medication delivery system 102 as needed (e.g., remotely regulate or control certain functions of the continuous medication delivery system 102). As another example, the gesture-based event detection system 104 may communicate the gesture data to one or more cloud computing systems or servers (such as a remote data processing system 116) for appropriate processing and handling in the manner described herein.

Similarly, an ancillary system 106 may include one or more sensors, detectors, measurement devices, and/or readers that obtain ancillary user status data that correlates to user activity, detectable behavior, eating habits, etc. In certain embodiments, an ancillary system 106 may include, cooperate with, or be realized as any of the following, without limitation: a heartrate monitor linked to the user; a blood pressure monitor linked to the user; a respiratory rate monitor linked to the user; a vital signs monitor linked to the user; an oxygen saturation monitor; an electrocardiogram (ECG or EKG) recorder that records timing and strength of the electrical signals that make the heart beat; a microphone; a thermometer (for the user's body temperature and/or the environmental temperature); a sweat detector linked to the user; an activity tracker linked to the user; a global positioning system (GPS); a clock, calendar, or appointment application linked to the user; a pedometer linked to the user; or the like. An ancillary system 106 may be configured and operated to communicate its output (user status data) to one or more components of the system 100 for analysis, processing, and handling in the manner described herein. In certain embodiments, user status data obtained from one or more ancillary systems 106 supplements the gesture data obtained from the gesture-based event detection system 104, such that user habits, physical behavior, and activity events are accurately and reliably detected.

In certain embodiments, the gesture-based event detection system 104, the continuous medication delivery system 102, and the discrete medication delivery system 103 are implemented as physically distinct and separate components, as depicted in FIG. 1. In such embodiments, the gesture-based event detection system 104 is external to the continuous medication delivery system 102 and/or the discrete medication delivery system 103 and is realized as an ancillary component, relative to the continuous medication delivery system 102 and/or the discrete medication delivery system 103. In accordance with alternative embodiments, however, the continuous medication delivery system 102 and/or the discrete medication delivery system 103 and the gesture-based event detection system 104 can be combined into a single hardware component or provided as a set of attached hardware devices. For example, the continuous medication delivery system 102 and/or the discrete medication delivery system 103 may include the gesture-based event detection system 104 or integrate the functionality of the system 104. Similarly, the analyte sensor 112 can be incorporated with the continuous medication delivery system 102, the discrete medication delivery system 103 or the gesture-based event detection system 104. These and other arrangements, deployments, and topologies of the system 100 are contemplated by this disclosure.

The at least one patient history and outcomes database 114 includes historical data related to the user's physical condition, physiological response to the medication regulated by the continuous medication delivery system 102 and/or the discrete medication delivery system 103, activity patterns or related information, eating patterns and habits, work habits, and the like. In accordance with embodiments where the continuous medication delivery system 102 and/or the discrete medication delivery system 103 is an insulin infusion device and the analyte sensor 112 is a glucose meter, sensor, or monitor, the database 114 can maintain any of the following, without limitation: historical glucose data and corresponding date/time stamp information; insulin delivery and dosage information; user-entered stress markers or indicators; gesture data (provided by the gesture-based event detection system 104) and corresponding date/time stamp information; ancillary user status data (provided by one or more ancillary systems 106) and corresponding date/time stamp data; diet or food intake history for the user; and any other information that may be generated by or used by the system 100 for purposes of controlling the operation of the continuous medication delivery system 102. In certain embodiments, the at least one patient history and outcomes database 114 can receive and maintain training data that is utilized to train, configure, and initialize the system 100 based on historical user behavior, physiological state, operation of the continuous medication delivery system 102 and/or the discrete medication delivery system 103, and user-identified activity events.

A patient history and outcomes database 114 may reside at a user device 108, at the continuous medication delivery system 102, at the discrete medication delivery system 103, at a data processing system 116, or at any network-accessible location (e.g., a cloud-based database or server system). In certain embodiments, a patient history and outcomes database 114 may be included with the patient care application 110. The patient history and outcomes database 114 enables the system 100 to generate recommendations, warnings, and guidance for the user and/or to regulate the manner in which the continuous medication delivery system 102 and/or the discrete medication delivery system 103 functions to administer therapy to the user, based on detected changes in the user's activity (which may be temporary, ongoing for an extended period of time, or somewhat permanent in nature).

Figure 6:
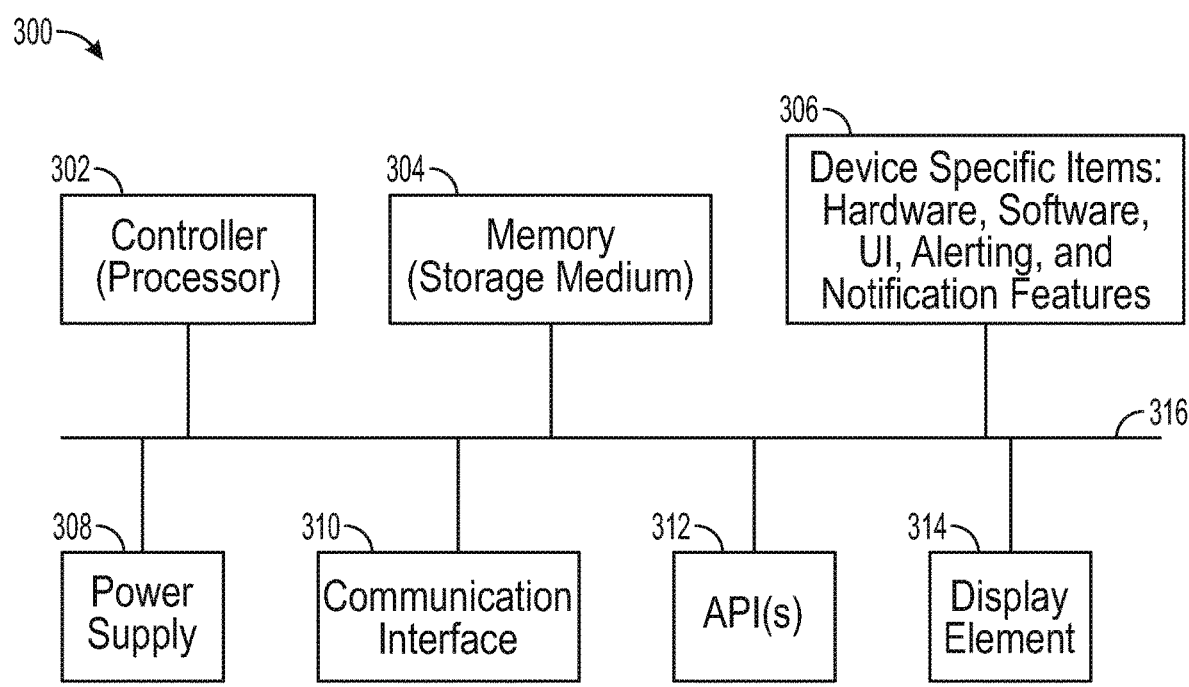
FIG. 6 is a block diagram representation of an exemplary embodiment of a computer-based or processor-based device suitable for deployment in the system shown in FIG. 1.

In accordance with certain embodiments, any or all of the components shown in FIG. 1 can be implemented as a computer-based or a processor-based device, system, or component having suitably configured hardware and software written to perform the functions and methods needed to support the features described herein. In this regard, FIG. 6 is a simplified block diagram representation of an exemplary embodiment of a computer-based or processor-based device 300 that is suitable for deployment in the system 100 shown in FIG. 1 (e.g., user device(s) 108).

The illustrated embodiment of the device 300 is intended to be a high-level and generic representation of one suitable platform. In this regard, any computer-based or processor-based component of the system 100 can utilize the architecture of the device 300. The illustrated embodiment of the device 300 generally includes, without limitation: at least one controller (or processor) 302; a suitable amount of memory 304 that is associated with the at least one controller 302; device-specific items 306 (including, without limitation: hardware, software, firmware, user interface (UI), alerting, and notification features); a power supply 308 such as a disposable or rechargeable battery; a communication interface 310; at least one application programming interface (API) 312; and a display element 314. Of course, an implementation of the device 300 may include additional elements, components, modules, and functionality configured to support various features that are unrelated to the primary subject matter described here. For example, the device 300 may include certain features and elements to support conventional functions that might be related to the particular implementation and deployment of the device 300. In practice, the elements of the device 300 may be coupled together via at least one bus or any suitable interconnection architecture 316.

The at least one controller 302 may be implemented or performed with a general purpose processor, a content addressable memory, a microcontroller unit, a digital signal processor, an application specific integrated circuit, a field programmable gate array, any suitable programmable logic device, discrete gate or transistor logic, discrete hardware components, or any combination designed to perform the functions described here. Moreover, the at least one controller 302 may be implemented as a combination of computing devices, e.g., a combination of a digital signal processor and a microprocessor, a plurality of microprocessors, one or more microprocessors in conjunction with a digital signal processor core, or any other such configuration.

The memory 304 may be realized as at least one memory element, device, module, or unit, such as: RAM memory, flash memory, EPROM memory, EEPROM memory, registers, a hard disk, a removable disk, a CD-ROM, or any other form of storage medium known in the art. In this regard, the memory 304 can be coupled to the at least one controller 302 such that the at least one controller 302 can read information from, and write information to, the memory 304. In the alternative, the memory 304 may be integral to the at least one controller 302. As an example, the at least one controller 302 and the memory 304 may reside in an ASIC. At least a portion of the memory 304 can be realized as a computer storage medium that is operatively associated with the at least one controller 302, e.g., a tangible, non-transitory computer-readable medium having computer-executable instructions stored thereon. The computer-executable instructions are configurable to be executed by the at least one controller 302 to cause the at least one controller 302 to perform certain tasks, operations, functions, and processes that are specific to the particular embodiment. In this regard, the memory 304 may represent one suitable implementation of such computer-readable media. Alternatively or additionally, the device 300 could receive and cooperate with computer-readable media (not separately shown) that is realized as a portable or mobile component or platform, e.g., a portable hard drive, a USB flash drive, an optical disc, or the like.

The device-specific items 306 may vary from one embodiment of the device 300 to another. For example, the device-specific items 306 will support: sensor device operations when the device 300 is realized as a sensor device; smartphone features and functionality when the device 300 is realized as a smartphone; activity tracker features and functionality when the device 300 is realized as an activity tracker; smart watch features and functionality when the device 300 is realized as a smart watch; medical device features and functionality when the device is realized as a medical device; etc. In practice, certain portions or aspects of the device-specific items 306 may be implemented in one or more of the other blocks depicted in FIG. 6.

If present, the UI of the device 300 may include or cooperate with various features to allow a user to interact with the device 300. Accordingly, the UI may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the device 300. The UI may include one or more graphical user interface (GUI) control elements that enable a user to manipulate or otherwise interact with an application via the display element 314. The display element 314 and/or the device-specific items 306 may be utilized to generate, present, render, output, and/or annunciate alerts, alarms, messages, or notifications that are associated with operation of the medication delivery system 102, associated with a status or condition of the user, associated with operation, status, or condition of the system 100, etc.

The communication interface 310 facilitates data communication between the device 300 and other components as needed during the operation of the device 300. In the context of this description, the communication interface 310 can be employed to transmit or stream device-related control data, patient-related user status (e.g., gesture data or status data), device-related status or operational data, sensor data, calibration data, and the like. It should be appreciated that the particular configuration and functionality of the communication interface 310 can vary depending on the hardware platform and specific implementation of the device 300. In practice, an embodiment of the device 300 may support wireless data communication and/or wired data communication, using various data communication protocols. For example, the communication interface 310 could support one or more wireless data communication protocols, techniques, or methodologies, including, without limitation: RF; IrDA (infrared); Bluetooth; BLE; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Moreover, the communication interface 310 could support one or more wired/cabled data communication protocols, including, without limitation: Ethernet; powerline; home network communication protocols; USB; IEEE 1394 (Firewire); hospital network communication protocols; and proprietary data communication protocols.

The at least one API 312 supports communication and interactions between software applications and logical components that are associated with operation of the device 300. For example, one or more APIs 312 may be configured to facilitate compatible communication and cooperation with the patient care application 110, and to facilitate receipt and processing of data from sources external to the device 300 (e.g., databases or remote devices and systems).

The display element 314 is suitably configured to enable the device 300 to render and display various screens, recommendation messages, alerts, alarms, notifications, GUIs, GUI control elements, drop down menus, auto-fill fields, text entry fields, message fields, or the like. Of course, the display element 314 may also be utilized for the display of other information during the operation of the device 300, as is well understood. Notably, the specific configuration, operating characteristics, size, resolution, and functionality of the display element 314 can vary depending upon the implementation of the device 300.

Figure 7:
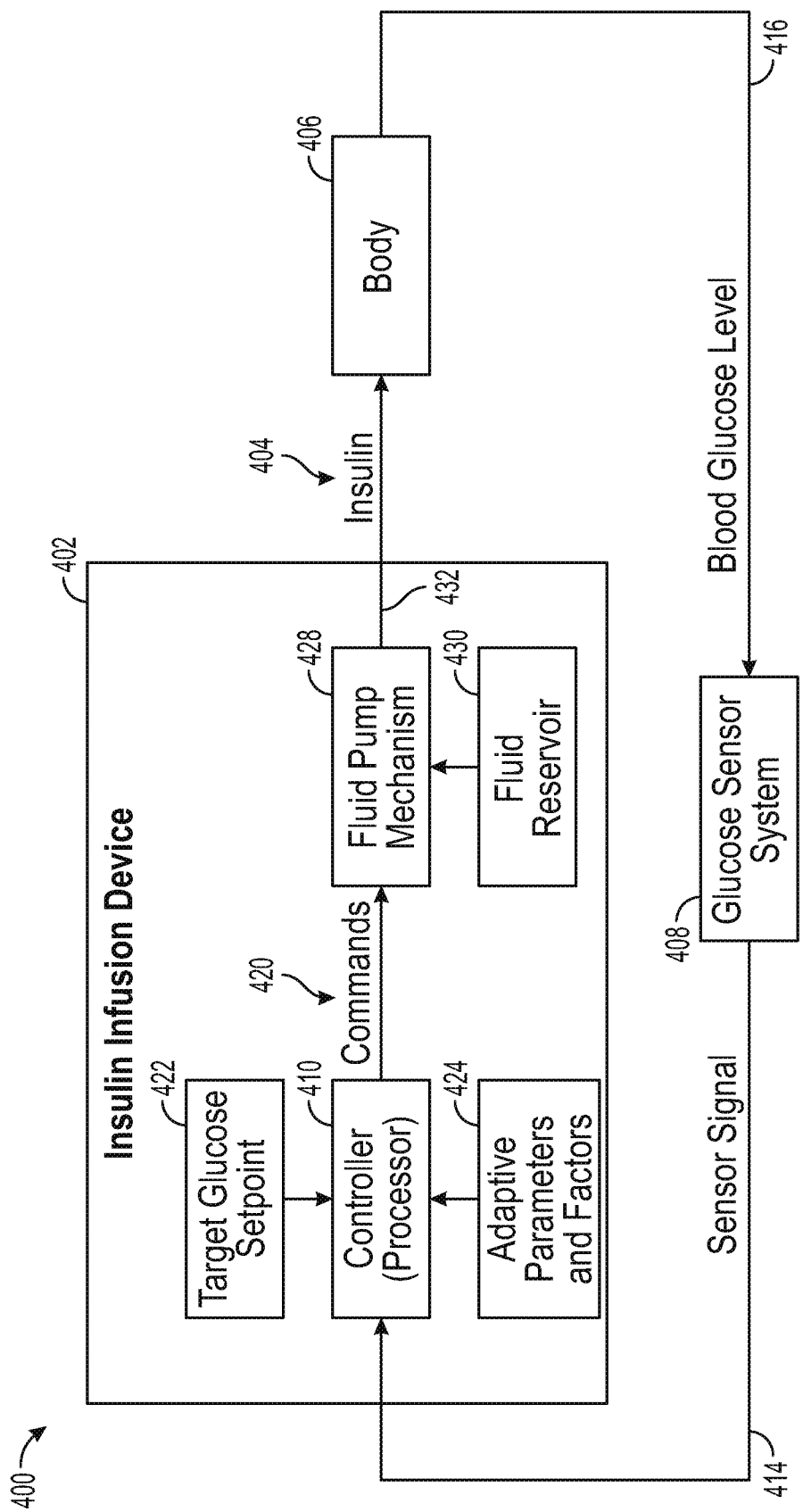
FIG. 7 is a block diagram representation of a closed loop glucose control system arranged in accordance with certain embodiments.

As mentioned above, the medication delivery system 102 is suitably configured and programmed to support an automatic mode to automatically control delivery of insulin to the user. In this regard, FIG. 7 is a simplified block diagram representation of a closed loop glucose control system 400 arranged in accordance with certain embodiments. The system 400 is one example of a system that can be used as part of the continuous medication delivery system 102 of FIG. 1. The system 400 depicted in FIG. 7 functions to regulate the rate of fluid infusion into a body of a user based on feedback from an analyte concentration measurement taken from the body. In particular embodiments, the system 400 is implemented as an automated control system for regulating the rate of insulin infusion into the body of a user based on a glucose concentration measurement taken from the body. The system 400 is designed to model the physiological response of the user to control an insulin infusion device 402 in an appropriate manner to release insulin 404 into the body 406 of the user in a similar concentration profile as would be created by fully functioning human β-cells when responding to changes in blood glucose concentrations in the body. Thus, the system 400 simulates the body's natural insulin response to blood glucose levels and not only makes efficient use of insulin, but also accounts for other bodily functions as well since insulin has both metabolic and mitogenic effects.

Certain embodiments of the system 400 include, without limitation: the insulin infusion device 402; a glucose sensor system 408 (e.g., the analyte sensor 112 shown in FIG. 1); and at least one controller 410, which may be incorporated in the insulin infusion device 402 as shown in FIG. 7. The glucose sensor system 408 generates a sensor signal 414 representative of blood glucose levels 416 in the body 406, and provides the sensor signal 414 to the at least one controller 410. The at least one controller 410 receives the sensor signal 414 and generates commands 420 that regulate the timing and dosage of insulin 404 delivered by the insulin infusion device 402. The commands 420 are generated in response to various factors, variables, settings, and control algorithms utilized by the insulin infusion device 402. For example, the commands 420 (and, therefore, the delivery of insulin 404) can be influenced by a target glucose setpoint value 422 that is maintained and regulated by the insulin infusion device 402. Moreover, the commands 420 (and, therefore, the delivery of insulin 404) can be influenced by any number of adaptive parameters and factors 424. The adaptive parameters and factors 424 may be associated with or used by: a therapy control algorithm of the insulin infusion device 402; a digital twin model of the patient, which can be used to recommend insulin dosages; a meal prediction algorithm; a user glucose prediction algorithm; or the like.

Generally, the glucose sensor system 408 includes a continuous glucose sensor, sensor electrical components to provide power to the sensor and generate the sensor signal 414, a sensor communication system to carry the sensor signal 414 to the at least one controller 410, and a sensor system housing for the electrical components and the sensor communication system. As mentioned above with reference to FIG. 6, the glucose sensor system 408 may be implemented as a computer-based or processor-based component having the described configuration and features.

Typically, the at least one controller 410 includes controller electrical components and software to generate commands for the insulin infusion device 402 based on the sensor signal 414, the target glucose setpoint value 422, the adaptive parameters and factors 424, and other user-specific parameters, settings, and factors. The at least one controller 410 may include a controller communication system to receive the sensor signal 414 and issue the commands 420.

Generally, the insulin infusion device 402 includes a fluid pump mechanism 428, a fluid reservoir 430 for the medication (e.g., insulin), and an infusion tube to infuse the insulin 404 into the body 406. In certain embodiments, the insulin infusion device 402 includes an infusion communication system to handle the commands 420 from the at least one controller 410, electrical components and programmed logic to activate the fluid pump mechanism 428 motor according to the commands 420, and a housing to hold the components of the insulin infusion device 402. Accordingly, the fluid pump mechanism 428 receives the commands 420 and delivers the insulin 404 from the fluid reservoir 430 to the body 406 in accordance with the commands 420. It should be appreciated that an embodiment of the insulin infusion device 402 can include additional elements, components, and features that may provide conventional functionality that need not be described herein. Moreover, an embodiment of the insulin infusion device 402 can include alternative elements, components, and features if so desired, as long as the intended and described functionality remains in place. In this regard, as mentioned above with reference to FIG. 6, the insulin infusion device 402 may be implemented as a computer-based or processor-based components having the described configuration and features, including the display element 214 or other device-specific items 206 as described.

The at least one controller 410 is configured and programmed to regulate the operation of the fluid pump mechanism 428 and other functions of the insulin infusion device 402. The at least one controller 410 controls the fluid pump mechanism 428 to deliver the fluid medication (e.g., insulin) from the fluid reservoir 430 to the body 406. As mentioned above, the at least one controller 410 can be housed in the infusion device housing, wherein the infusion communication system is an electrical trace or a wire that carries the commands 420 from the at least one controller 410 to the fluid pump mechanism 428. In alternative embodiments, the at least one controller 410 can be housed in the sensor system housing, wherein the sensor communication system is an electrical trace or a wire that carries the sensor signal 414 from the sensor electrical components to the at least one controller 410. In accordance with some embodiments, the at least one controller 410 has its own housing or is included in a supplemental or ancillary device. In other embodiments, the at least one controller 410, the insulin infusion device 402, and the glucose sensor system 408 are all located within one common housing.

Referring again to FIG. 1, the gesture-based event detection system 104 employs at least one sensor to obtain corresponding user-specific sensor data. The obtained user-specific sensor data is processed or analyzed by the gesture-based event detection system 104 and/or by another suitably configured device or component of the system 100 to determine whether the user's current behavior reflects a significant or measurable change in activity, relative to a currently implemented, active, or monitored therapy behavior pattern of the user. The obtained user-specific sensor data may also be processed or analyzed to obtain certain activity-related parameters, characteristics, and/or metadata for the user. For example, the obtained user-specific sensor data may identify, include, or indicate any or all of the following, without limitation: timestamp data corresponding to the occurrence of detected events; a type, category, or classification of the detected physical behavior or activity; location data; user posture or position information; etc.

The gesture-based event detection system 104 may include, cooperate with, or be realized as a motion-based physical behavior detection system, an activity-based physical behavior detection system, an image or video-based activity detection system, or the like. In certain embodiments, the system 104 may be realized as a unitary "self-contained" wearable system that communicates with one or more other components of the system 100. For example, the system 104 can be implemented with at least one wearable device such as an activity monitor device, a smart watch device, a smart bracelet or wristband device, or the like. In some embodiments, the system 104 may be realized as at least one portable or wearable device that includes or communicates with one or more external or ancillary sensor devices, units, or components. For example, the system 104 can be implemented with a wearable or portable smart device that is linked with one or more external sensors worn or carried by the user. These and other possible deployments of the system 104 are contemplated by this disclosure. In this regard, United States patent publication number US 2020/0135320 and United States patent publication number US 2020/0289373 disclose gesture-based event detection systems that are suitable for use as the system 104; the entire content of these United States patent documents is incorporated by reference herein.

Figure 8:
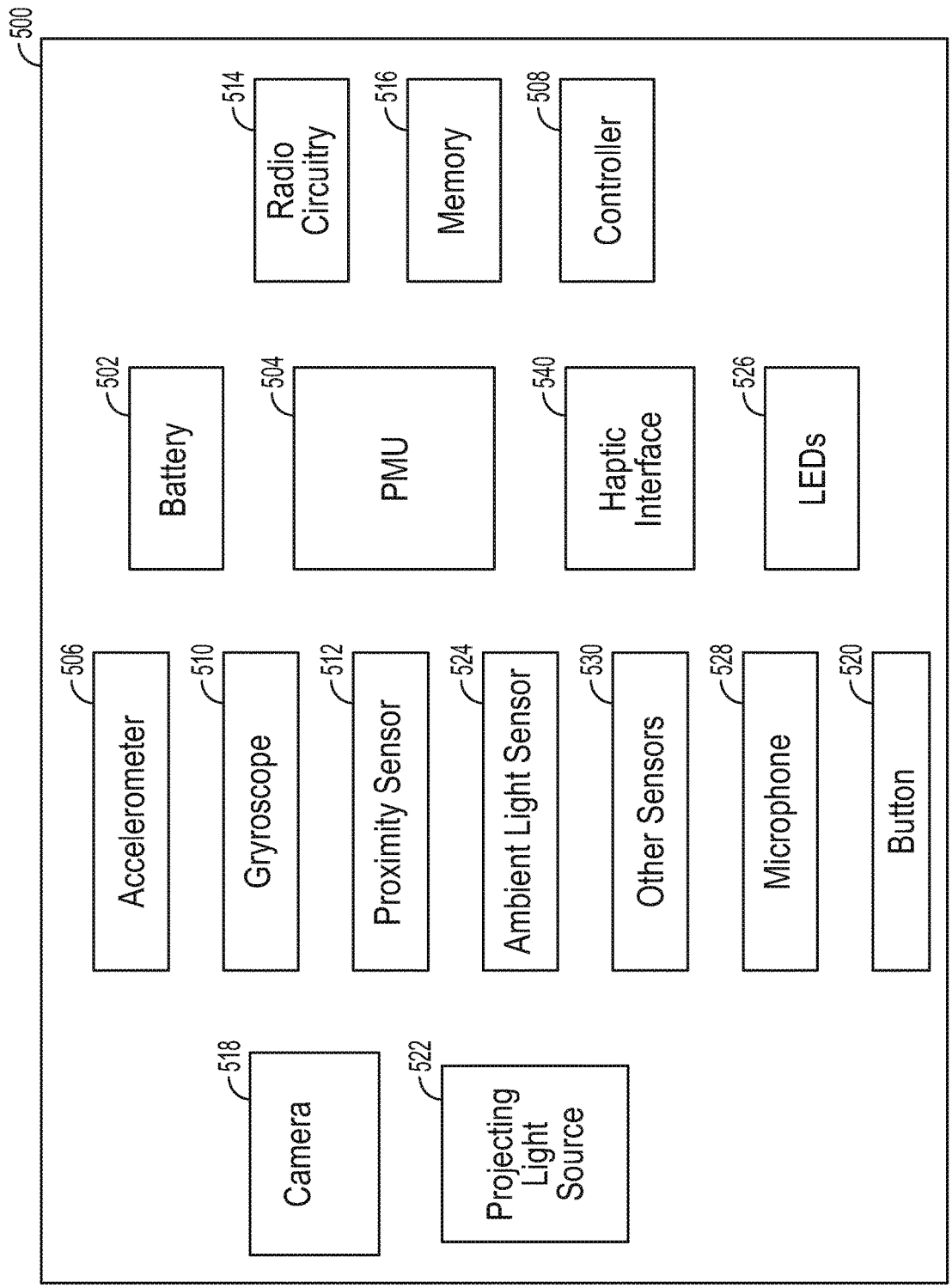
FIG. 8 is a block diagram representation of a gesture-based event detection system arranged in accordance with certain embodiments.

FIG. 8 is a block diagram representation of a gesture-based event detection system 500 arranged in accordance with certain embodiments. The system 500 is suitable for use with the system 100 shown FIG. 1. Some or all components of the gesture-based event detection system 500 can be used to implement the gesture-based event detection system 104 of FIG. 1. In certain embodiments, the system 500 is deployed as a wearable electronic device in the form factor of a bracelet or wristband that is worn around the wrist or arm of a user's dominant hand. The system 500 may optionally be implemented using a modular design, wherein individual components or elements include one or more subsets of the disclosed components and overall functionality. The user may choose to add specific components or elements based on personal preferences and requirements.

The system 500 includes a battery 502 and a power management unit (PMU) 504 to deliver power at the proper supply voltage levels to all electronic circuits and components. The PMU 504 may also include battery-recharging circuitry. The PMU 504 may also include hardware, such as switches, that allows power to specific electronics circuits and components to be cut off when not in use.

When there is no movement-based or gesture-based behavior event in progress, most circuitry and components in the system 500 are switched off to conserve power. Only circuitry and components that are required to detect or help predict the start of a behavior event of interest may remain enabled. For example, if no motion is being detected, all sensor circuits but an accelerometer 506 may be switched off and the accelerometer 506 may be put in a low-power wake-on-motion mode or in another lower power mode that consumes less power and uses less processing resources than its high performance active mode. A controller 508 of the system 500 may also be placed into a low-power mode to conserve power. When motion or a certain motion pattern is detected, the accelerometer 506 and/or the controller 508 may switch into a higher power mode and additional sensors such as, for example, a gyroscope 510 and/or a proximity sensor 512 may also be enabled. When a potential start of a movement-based or gesture-based event is detected, memory variables for storing event-specific parameters, such as gesture types, gesture duration, etc. can be initialized.

In another example, upon detection of user motion, the accelerometer 506 switches into a higher power mode, but other sensors remain switched off until the data from the accelerometer 506 indicates that the start of a behavior event has likely occurred. At that point in time, additional sensors such as the gyroscope 510 and the proximity sensor 512 may be enabled.

In another example, when there is no behavior event in progress, both the accelerometer 506 and gyroscope 510 are enabled but at least one of either the accelerometer 506 or the gyroscope 510 is placed in a lower power mode compared to their regular power mode. For example, the sampling rate may be reduced to conserve power. Similarly, the circuitry required to transfer data from the system 500 to a destination device may be placed in a lower power mode. For example, radio circuitry 514 could be disabled. Similarly, the circuitry required to transfer data from the system 500 may be placed in a lower power mode. For example, the radio circuitry 514 could be disabled until a possible or likely start of a behavior event has been determined. Alternatively, it may remain enabled but in a low power state to maintain the connection between the system 500 and one or more other components of the system 100, but without transferring user status data, sensor data, or the like.

In yet another example, all motion-detection related circuitry may be switched off if, based on certain metadata, it is determined that the occurrence of a particular behavior event, such as a food intake event, is unlikely. This may be desirable to further conserve power. Metadata used to make this determination may, among other things, include one or more of the following: time of the day, location, ambient light levels, proximity sensing, and detection that the system 500 has been removed from the wrist or hand, detection that the system 500 is being charged, or the like. Metadata may be generated and collected by the system 500. Alternatively, metadata may be collected by another device that is external to the system 500 and is configured to directly or indirectly exchange information with the system 500. It is also possible that some metadata is generated and collected by the system 500, while other metadata is generated and collected by a device that is external to the system 500. In case some or all of the metadata is generated and collected external to the system 500, the system 500 may periodically or from time to time power up its radio circuitry 514 to retrieve metadata related information from another device.

In certain embodiments, some or all of the sensors may be turned on or placed in a higher power mode if certain metadata indicates that the occurrence of a particular behavior event, such as the user beginning to work, jog, or eat, is likely. Metadata used to make this determination may, among other things, include one or more of the following: time of the day; location; ambient light levels; proximity sensing; historical user behavior patterns. Some or all of the metadata may be collected by the system 500 or by an ancillary device that cooperates or communicates with the system 500, as mentioned above.

User status data used to track certain aspects of a user's behavior may be stored locally inside memory 516 of the system 500 and processed locally using the controller 508 of the system 500. User status data may also be transferred to the medication delivery system 102, the patient care application 110, and/or one or more of the database 114 mentioned above with reference to FIG. 1 (such that the user status data can be processed, analyzed, or otherwise utilized by the applications or components that receive the user status data). It is also possible that some of the processing and analysis are performed locally by the system 500, while further processing and analysis are performed by one or more other components of the system 100.

The detection of the start of a behavior event, such as the start of a work activity, may trigger the power up and/or activation of additional sensors and circuitry, such as a camera 518. Power up and/or activation of additional sensors and circuitry may occur at the same time as the detection of the behavior event of interest or some time thereafter. Specific sensors and circuitry may be turned on only at specific times during a detected event, and may be switched off otherwise to conserve power. It is also possible that the camera 518 only gets powered up or activated upon explicit user intervention such as, for example, pushing and holding a button 520. Releasing the button 520 may turn off the camera 518 to conserve power.

When the camera 518 is powered up, a projecting light source 522 may also be enabled to provide visual feedback to the user about the area that is within view of the camera or to otherwise illuminate the field of view. Alternatively, the projecting light source 522 may only be activated sometime after the camera 518 has been activated. In certain cases, additional conditions may need to be met before the projecting light source 522 is activated. Such conditions may include: the determination that the projecting light source 522 is likely aiming in the direction of the object of interest; the determination that the system 500 is not moving excessively; or the like. In some embodiments, one or more light emitting diodes (LEDs) 526 may be used as the projecting light source 522.

Images may be tagged with additional information or metadata such as: camera focal information; proximity information from the proximity sensor 512; ambient light levels information from an ambient light sensor 524; timestamp information; etc. Such additional information or metadata may be used during the processing and analysis of the user status data.

The projecting light source 522 may also be used to communicate other information. As an example, an ancillary device may use inputs from one or more proximity sensors 512, process those inputs to determine if the camera 518 is within the proper distance range from the object of interest, and use one or more light sources to communicate that the camera is within the proper distance range, that the user needs to increase the distance between camera and the object of interest, or that the user needs to reduce the distance between the camera and the object of interest.

The projecting light source 522 may also be used in combination with the ambient light sensor 524 to communicate to the user if the ambient light is insufficient or too strong for an adequate quality image capture. The projecting light source 522 may also be used to communicate information including, but not limited to, a low battery situation or a functional defect.

The projecting light source 522 may also be used to communicate dietary coaching information. As an example, the projecting light source 522 might, among other things, indicate if not enough or too much time has expired since a previous food intake event, or may communicate to the user how he/she is doing against specific dietary goals.

Signaling mechanisms to convey specific messages using one or more projecting light sources 522 may include, but are not limited to, one or more of the following: specific light intensities or light intensity patterns; specific light colors or light color patterns; specific spatial or temporal light patterns. Multiple mechanisms may also be combined to signal one specific message.

A microphone 528 may be used by the user to add specific or custom labels or messages to a detected event and/or image. In certain embodiments, audio captured by the microphone 528 can be processed to assist in the determination of whether the user is eating, drinking, commuting, exercising, working, or resting. Audio snippets may be processed by a voice recognition engine.

In certain embodiments, the accelerometer 506 (possibly combined with other sensors, including other inertial sensors) may, in addition to tracking at least one parameter that is directly related to a gesture-based behavior event, also be used to track one or more parameters that are not directly related to that particular event. Such parameters may, among other things, include physical activity, sleep, stress, or illness.

In addition to the particular sensors, detectors, and components mentioned above, the system 500 may include or cooperate with any number of other sensors 530 as appropriate for the particular embodiment. For example, and without limitation, the system 500 may include or cooperate with any or all of the following: a heartrate monitor; a physiological characteristic or analyte sensor; a continuous glucose monitor; a GPS receiver; and any other sensor, monitor, or detector mentioned elsewhere herein. The system 500 obtains user status data from one or more of its sensors, detectors, and sources, wherein the user status data indicates a stressful activity of the user. The user status data can be analyzed and processed by the system 500 (and/or by one or more other components of the system 100) to determine whether the user's current behavior is consistent with normally expected behavior or activity. In certain embodiments, the system 500 and/or an ancillary system 106 or device determines the user's activity and related behavior primarily based on the output of user-worn motion sensors, movement sensors, one or more inertial sensors (e.g., one or more accelerometers and/or one or more gyroscopes), one or more GPS sensors, one or more magnetometers, one or more force or physical pressure sensors, or the like, which are suitably configured, positioned, and arranged to measure physical movement or motion of the user's limbs, digits, joints, facial features, head, and/or other body parts.

In some embodiments, the system 500 includes at least one haptic interface 540 that is suitably configured and operated to provide haptic feedback as an output. The at least one haptic interface 540 generates output(s) that can be experienced by the sense of touch by the user, e.g., mechanical force, vibration, movement, temperature changes, or the like. Haptic feedback generated by the at least one haptic interface 540 may represent or be associated with one or more of the following, without limitation: reminders; alerts; confirmations; notifications; messages; numerical values (such as measurements); status indicators; or any other type of output provided by the system 500.

In certain embodiments, the user status data (e.g., sensor data) is provided to a gesture recognizer unit or processor. To this end, sensor data may be sent in raw format. Alternatively, a source of sensor data may perform some processing (e.g., filtering, compression, or formatting) on raw sensor data before sending the processed sensor data to the gesture recognizer unit. The gesture recognizer unit analyzes the incoming sensor data and converts the incoming sensor data into one or more streams of corresponding gestures, which may be predetermined or otherwise classified or categorized. The gesture recognizer unit may use one or more ancillary inputs (such as the output from one or more ancillary systems 106) to aid in the gesture determination process. Nonlimiting examples of an ancillary input include: time of day; the probability of a specific gesture occurring based on statistical analysis of historical gesture data for that user; geographical location; heart rate; other physiological sensor inputs. Other ancillary inputs are also possible.

The output of the gesture recognizer unit—the detected gestures—can be sent to an event detector or processor. The event detector analyzes the incoming stream of gestures to determine if the start of an event of interest (e.g., eating a meal, going to bed, working out) has occurred, whether an event is ongoing, whether an event has ended, or the like. Although this description mentions meal detection, the gesture-based event detection system 500 may be suitably configured to monitor other types of physical behavior or activities. Such activities include, without limitation: reading; sleeping; smoking; getting dressed; driving; walking; commuting; working; exercising; turning down a bed; making a bed; brushing teeth; combing hair; talking on the phone; inhaling or injecting a medication; and activities related to hand hygiene or personal hygiene.

Figure 9:
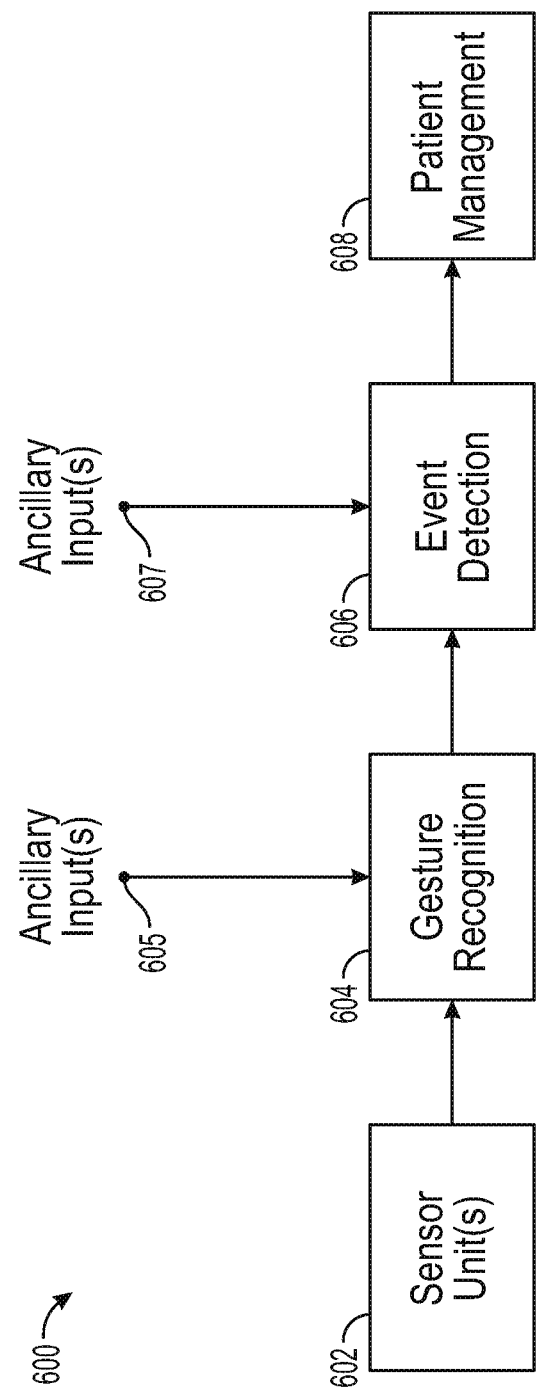
FIG. 9 is a block diagram representation of an embodiment of a gesture-informed patient management system in accordance with certain embodiments.

FIG. 9 is a simplified block diagram representation of an embodiment of a gesture-informed patient management system 600. The depicted patient management system 60 includes, without limitation, one or more sensor units 602, a gesture recognition unit 604, an event detection unit 606, and a patient management unit 608. Some or all components of the gesture-informed patient management system 600 can be used to implement the gesture-based event detection system 104 of FIG. 1.

The sensor unit(s) 602 generally represent the sensor(s) embedded in, integrated with, or otherwise associated with one or more portable or wearable devices associated with a patient, such as, for example, an activity tracker, a smart watch, a wristband, a ring, a mobile phone, or a portable electronic medical device (e.g., a continuous glucose monitoring device, an infusion device, an injection pen, and/or the like). For example, in one or more exemplary embodiments, the sensor unit(s) 602 include an accelerometer (e.g., accelerometer 506) and a gyroscope (e.g., gyroscope 510) associated with a smart watch. That said, it should be appreciated the patient management system 600 is not limited to any particular type, configuration, or number of sensor unit(s) 602, and in practice, the sensor unit(s) 602 may include one or more of the following sensing arrangements: accelerometers, gyroscopes, magnetometers, image sensors, cameras, optical sensors, proximity sensors, pressure sensors, odor sensors, gas sensors, Global Positioning Systems (GPS) receivers, microphones, galvanic skin response sensors, thermometers, ambient light sensors, UV sensors, electrodes for electromyographic ("EMG") potential detection, bio-impedance sensors, spectrometers, glucose sensors, heart rate sensors, pulse sensors, touchscreen or capacitive sensors. In this regard, the output of the sensor unit(s) 602 may include any sort of motion data, location data, physiological data (e.g., temperature, heart rate, pulse, galvanic skin response, blood or body chemistry, and/or the like), or other sensor data depending on the sensor type. The output of the sensor unit(s) 602 may be communicated to the gesture recognition unit 604 wirelessly or via wires, in analog or digital form, directly or indirectly (e.g., intermediated by gating and/or clocking circuits, analog-to-digital converters, and/or the like).

The gesture recognition unit 604 generally represents a software application or component of the patient management system 600 that receives the sensor data signals from the sensor unit(s) 602 and analyzes the received sensor data to detect or otherwise identify gestures performed by the patient based on the received sensor data. In this regard, a gesture generally represents a discrete set of one or more physical movements having associated spatial and/or temporal characteristics that are distinguishable from other gestures. For example, as described in United States Patent Publication Number 2020/0289373, the gesture recognition unit 604 may utilize machine learning or other artificial techniques to map different subsets of sensor data within one or more streams of received sensor data to different gesture features, which, in turn, are then analyzed to classify or otherwise resolve the different subsets of the sensor data and corresponding gesture features into a particular combination or sequence of gestures performed by the patient. In one or more embodiments, the gesture recognition unit 604 fuses or otherwise combines concurrent or otherwise temporally-associated accelerometer data and gyroscope data to obtain an orientation vector, with the concurrent or temporally-associated combinations of accelerometer data, gyroscope data, and fused orientation vectors being input to a feature generator, which, in turn, generates a corresponding stream of gesture features, which, in turn are input to the gesture recognition model which classifies or otherwise resolves one or more streams of gesture features into corresponding gestures. In exemplary embodiments, the gesture recognition unit 604 also associates or otherwise assigns a confidence metric to each gesture based on the gesture features. In this regard, for a given stream of sensor data received by the gesture recognition unit 604, the gesture recognition unit 604 outputs a corresponding stream of gestures and associated confidence levels.

In some embodiments, the gesture recognition unit 604 receives one or more ancillary inputs 605 which may influence the gesture detection or the confidence or probability assigned to detected gestures. For example, the ancillary input 605 may include operational contextual data, such as, the current time of day, the current day of the week, the current month of the year, the current location of the patient, and/or the like, along with other patient-specific data such as historical gesture data associated with the patient, a patient profile associated with the patient or other patient-specific personalization that may be utilized by the gesture recognition unit 604 to influence manner in which particular gesture features are mapped to a gesture for the particular patient. In this regard, statistical analysis of the historical gesture data and potentially other patient-specific data may be utilized to determine or otherwise assign probabilities of a specific gesture occurring based on the current operational context. It should be noted that there are any number of different types of ancillary input data that may be correlative to the occurrence or non-occurrence of a particular gesture, and the subject matter described herein is not limited to any particular type or combination of ancillary inputs 605 that may be utilized by the gesture recognition unit 604.

In one or more embodiments, the executable code or programming instructions corresponding to the gesture recognition unit 604 is stored or otherwise maintained in a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by a processor or other processing system. For example, in one or more exemplary embodiments, the computer-executable programming instructions corresponding to the gesture recognition unit 604 are stored in a data storage element (e.g., memory 416) of a wearable electronic device including the sensor unit(s) 602, and, when read and executed by a processing system (e.g., controller 408) of the wearable electronic device, the instructions cause the wearable electronic device to generate the gesture recognition unit 604 at the wearable electronic device. In this regard, in some embodiments, the wearable electronic device may transmit or otherwise provide signals or data indicating one or more streams of detected gestures and associated confidence levels to another device for further processing and/or analysis. That said, in other embodiments, the gesture recognition unit 604 may be implemented at or on a patient's mobile phone or other portable electronic device (e.g., user device 108) that receives sensor data signals from the sensor unit(s) 602 via a wireless network, or be implemented at or on a cloud computing system or remote server that receives the sensor data signals from the sensor unit(s) 602 via the Internet, a cellular network, or the like.

Still referring to FIG. 9, the event detection unit 606 generally represents a software application or component of the patient management system 600 that receives the detected gestures and confidence levels from the from the gesture recognition unit 604 and analyzes the received gesture data to detect or otherwise identify events or activities performed by the patient based on the received gesture data. For example, as described in United States Patent Publication Number 2020/0289373, the event detection unit 606 may utilize machine learning or other artificial techniques to map one or more streams of detected gestures and associated confidence levels into a particular event or activity being performed by the patient based on the type of gestures detected, the sequence of detected gestures, the temporal relationship between gestures and/or the confidence metrics assigned to the detected gestures. In this manner, the event detection unit 606 may map lower-level gestures into a higher-level physical behavior while filtering or otherwise deemphasizing false positives or spurious gestures. Thus, for a given stream of detected gestures received by the event detection unit 606, the event detection unit 606 outputs an indication of a detected event or activity by the patient and an associated confidence or probability metric for the event. For example, for a sequence of detected food intake gestures may be mapped or otherwise recognized as a food intake event having a particular start time, pace, duration, and/or the like with an assigned level of confidence or probability influenced by the confidence associated with the detected food intake gestures and potentially other factors.

In a similar manner as described for the gesture recognition unit 604, the event detection unit 606 may receive ancillary input 607 which may influence the event detection or the confidence or probability assigned to detected events. For example, the ancillary input 607 may include event log data associated with the patient that maintain data pertaining to historical events or activities by the patient (e.g., meals, exercise, sleep, boluses, glucose excursion events, and/or the like), with statistical analysis of the historical event log data and potentially other patient-specific data being utilized to determine or otherwise assign probabilities of a specific event occurring based on the current operational context. In this regard, if the patient habitually engages in meals at or around a certain time of day, food intake gestures occurring at that time of day consistent with the patient's historical behavior may be more likely to be mapped to a meal event or other food intake event, or the detected meal event or food intake event may be assigned a higher probability or confidence value based on the consistency with the patient's historical behavior. Again, it should be noted that there are any number of different types of ancillary input data that may be correlative to the occurrence or non-occurrence of a particular event, and the subject matter described herein is not limited to any particular type or combination of ancillary inputs 607 that may be utilized by the event detection unit 606.

In one or more embodiments, the executable code or programming instructions corresponding to the event detection unit 606 is stored or otherwise maintained in a data storage element or memory, including any sort of short or long term storage media or other non-transitory computer-readable medium, which is capable of storing programming instructions for execution by a processor or other processing system. For example, in one or more exemplary embodiments, the computer-executable programming instructions corresponding to the event detection unit 606 are stored in a data storage element (e.g., memory 516) of a wearable electronic device including the sensor unit(s) 602, and, when read and executed by a processing system (e.g., controller 508) of the wearable electronic device, the instructions cause the wearable electronic device to generate the event detection unit 606 at the wearable electronic device. In this regard, in some embodiments, the wearable electronic device may transmit or otherwise provide signals or data indicating one or more streams of detected events and associated confidence or probability levels to another device for further processing and/or analysis. That said, in other embodiments, the event detection unit 606 may be implemented at or on a patient's mobile phone or other portable electronic device (e.g., user device 108) or on a cloud computing system or remote server that receives gesture data signals from the gesture recognition unit 604 implemented at another device via a network.

Still referring to FIG. 9, the patient management unit 608 generally represents a software application or component of the patient management system 600 that receives the detected event data from the event detection unit 606 and automatically initiates or otherwise performs one or more actions with respect to management of the patient's physiological condition. In some embodiments, the patient management unit 608 is configurable to support one or more autonomous operating modes for an infusion device, a smart pen, or other fluid delivery device, where the patient management unit 608 calculates or otherwise determines dosage commands for operating an actuation arrangement to deliver fluid to the patient. For example, in a closed-loop operating mode, the patient management unit 608 may determine a dosage command based at least in part on a current glucose measurement value for the patient in a manner that is influenced by an event detected by the event detection unit 606. In some embodiments, the patient management unit 608 is configurable to generate or otherwise provide user notifications or alerts via a user interface element based at least in part on a detected event. In this regard, the patient management 608 application may utilize patient-specific settings, preferences, or other notification criteria to automatically generate user notifications in a manner that is influenced by the detected event and potentially other factors (e.g., the patient's current or recent sensor glucose measurement values).

In one or more embodiments, the executable code or programming instructions corresponding to the patient management unit 608 is stored or otherwise maintained at one of the patient's associated devices (e.g., the patient's mobile phone, the patient's infusion device or other fluid delivery device, or the like) or at a cloud computing system or remote server. For example, the patient management unit 608 executing on the patient's phone may receive or otherwise obtain signals or data indicating detected gestures and/or events from the patient's smart watch or other wearable device, analyze the received data, and transmit or otherwise provide dosage commands or signals influenced by the detected gestured-based events to the patient's infusion device (e.g., via a wireless network) to automatically operate the infusion device to deliver insulin or another fluid or medicament to account for the detected event(s), or the patient management unit 608 may generate GUI displays or other user notifications influenced by the detected event(s) at the mobile device. That said, in other embodiments, when the patient management unit 608 is implemented at a remote server or other cloud computing system, the patient management unit 608 may transmit or otherwise provide dosage commands or signals to a device associated with the patient via a network. In yet other embodiments, the patient management unit 608 may be implemented at the patient's medical device and receive detected event data from the patient's mobile device, the patient's wearable device, or a remote server or other cloud computing system. In this regard, depending on the embodiment, the various units 604, 606, 608 may be distributed across one or more different devices 102, 103, 104, 106, 108, 111, 112, 114, 116 in a system 100 and the subject matter described herein is not limited to any particular implementation.

Figure 10:
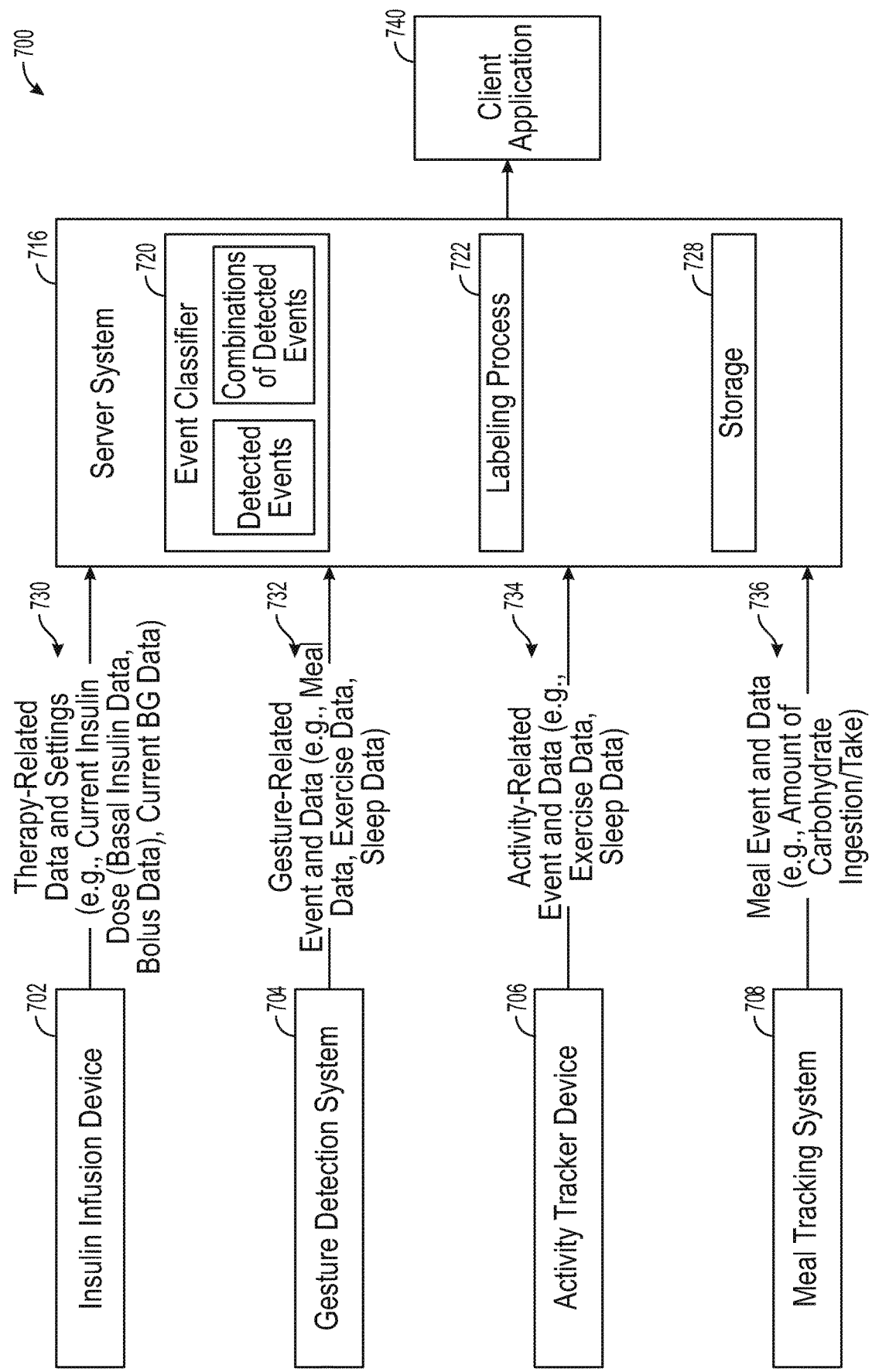
FIG. 10 is a block diagram illustrating a system in accordance with certain embodiments.

FIG. 10 is a block diagram illustrating a system 700 in accordance with certain embodiments. The system 700 can include an insulin infusion device 702 of a user, a gesture detection system 704, a gesture detection device 706, a meal tracking system 708, a server system 716, and a client application 740.

The insulin infusion device 702 can be implemented using any of the continuous insulin therapy system 102 and discrete insulin therapy system 103 described with respect to FIG. 1, the smart insulin pen 160 described with respect to FIG. 3B, the smart pen accessory 170 described with respect to FIG. 4, the injection pen 200 described with respect to FIG. 5. The insulin infusion device 702 can also be implemented in conjunction with an analyte sensor (not illustrated), such as the analyte sensor 112 described with respect to FIG. 1, the glucose sensor system 408 described with respect to FIG. 7 and/or a continuous glucose monitoring device of FIG. 9. The gesture detection system 704, the activity tracker device 706, and the meal tracking system 708 can be some of the components of the event detection system 107 described with respect to FIG. 1, the gesture-based event detection system 500 described with respect to FIG. 8, the gesture-informed patient management system 600 described with respect to FIG. 9. The gesture detection system 704, the activity tracker device 706, and the meal tracking system 708 are non-limiting examples of the systems and devices that can be part of the event detection system 107 of FIG. 1. Although not illustrated, the system 700 can also include other systems and components that can be part of the event detection system 107 of FIG. 1, the gesture-based event detection system 500 of FIG. 8, and the gesture-informed patient management system 600 of FIG. 9. The server system 716 (having an event classifier 720, a labeling process 722, storage 728) can be implemented using any of the event classification service 111, the database 114 and the data processing system 116 described with respect to FIG. 1. These devices, systems and models are described with reference to FIGS. 1-9, and for sake of brevity, the description of these devices, systems and models will not be repeated.

The client application 740 can be implemented at the server system 716 or at another computer-based system that is distinct from the server system 716. The system 700 can be used to classify events detected by the insulin infusion device 702, the gesture detection system 704, the activity tracker device 706, and/or the meal tracking system 708 as labeled events and/or labeled event combinations. These labeled events and/or labeled event combinations can be processed at a client application 740.

The server system 716 receives input data for different detected events. As used herein, an "event" can refer to a specific condition or physical activity that is detectable and indicative of a physical behavior of a user (or that is associated with a physical behavior of a user). Events can be input by a user, measured or detected by a sensor-based system, or estimated or predicted by a model or system, such as a mathematical model or artificial intelligence (AI) based system. In addition, events can be recorded in a database and later used for the various purposes described herein. Each event can potentially impact physiological glucose dynamics of the user and can be correlated to a change in an insulin demand of the user and/or blood glucose levels of the user. As will be explained in greater detail below, the input data for detected events can include data regarding a specific condition or physical activity that is detectable and indicative of a physical behavior of the user.

Non-limiting examples of specific conditions or activities that are indicative of the physical behavior of the user can include, but are not limited to, for example, meal ingestion events and related data that describes such events including meal timing, meal duration, meal content, amounts of calories or macronutrients consumed by the user as part of a meal, etc.; sleep events and related data that describes such events including timing, duration, quality of sleep, etc.; physical activity events and related data that describes such events including timing of physical activity, duration of physical activity, exertion levels and patterns that describe physical activity, intensity levels and patterns that describe physical activity, etc.; exercise events and related data that describes such events including timing, duration, amounts, intensity, etc. and work-related events and related data that describes such events including timing, duration, amounts, intensity, etc.

For example, in accordance with the embodiment illustrated in FIG. 10, the input data for detected events can include therapy-related data, parameters and settings 730 from the insulin infusion device 702 of a user, which can include, for example, current insulin data and current blood glucose data; gesture-related event data 732 from the gesture detection system 704, which can include meal data, exercise data, sleep data, etc.; activity-related data 734 detected using the activity tracker device 706, which can include physical activity data, exercise data, sleep data, etc.; meal event data 736 from the meal tracking system 708, which can include carbohydrate intake data for the user; user entered carbohydrate intake data for the user (e.g., entered into insulin pump to generate a meal correction bolus).

In some cases, events can include, for example, events from an insulin therapy system such as therapy-related data, parameters and settings 730 associated with operation of the insulin infusion device. Therapy-related data can include data related to the status of the infusion device and/or the status of the user. Some non-limiting examples of therapy-related data can include, but are not limited to: sensor glucose data associated with glucose levels of the user; meal data associated with meals announced by the user; insulin delivery data, including basal insulin and insulin bolus amounts, along with their associated time data (time/date stamps); announced meal time data or information; carbohydrate intake data for a user including carbohydrate intake estimates for announced meals; the insulin sensitivity factor (ISF) associated with operation of the device in the manual insulin delivery mode; an insulin to carbohydrate (I:C) ratio value or equivalently a carbohydrate to insulin (C:I) ratio value; and user-entered blood glucose meter measurements. The therapy-related data can also include, for example, closed-loop pump data including, but not limited to: settings from an insulin infusion device of a user; data indicating basal insulin delivered by the insulin infusion device to the user during operation in the automated closed-loop insulin delivery mode for at least one defined period of time; data that indicates the total amount of insulin delivered by the infusion device during at least one defined period of time (e.g., the last 24 hours, a number of sequential segments of time, etc.), such as the average total daily dose (TDD) of insulin for the user; glucose sensor data, log data for the infusion device, user-input data, time/calendar data associated with certain events or collected data, and/or other information.

Events can also include many other types of information, and can be detected or be determined based on various types of data from detection systems or devices, such as a gesture detection device. Examples of such data can include, but not limited to: accelerometer (x,y,z) data, geolocation data, iBeacon location data, skin temperature data, ambient air temperature data, bioimpedance heart rate data, sweat data (e.g., GSR-conductance), blood pressure data, shake detection data, pedometer data, barometer data, gyroscope data, meal log data, orientation data (e.g., azimuth, pitch, roll (degrees)); health kit data (such as data from Apple® Healthkit, Google® Fit, etc.), medication/prescription information data, user gestures data, UV light detector data, magnetometer data, respiration data, muscle activity data, pulse oximeter data, blood and interstitial fluid pH data, METS data, sleep quality/time data, EMR and lab data, etc.

The detected events can be stored and processed at the server system 716. The server system 716 can group the detected events into different combinations of detected events. The detected events and different combinations of detected events can then be further processed at an event classifier 720 and labeling process 722 as will be described below.

Each detected event (or impact of that physical behavior) can potentially impact physiological glucose dynamics of the user. An event can be correlated, for example, to a change in one or more of an insulin demand of the user and/or blood glucose levels of the user. Each detected event (or combination of detected events) can be associated with a probability of a decreased insulin delivery demand, a probability of an increased insulin delivery demand for that event (or particular combination of detected events), or a probability that insulin delivery demand will not change.

In this embodiment, the event classifier 720 can classify each detected event and each combination of detected events by mapping that detected event or combination of detected events to a probability of an increased insulin delivery demand, a probability of a decreased insulin delivery demand, or a probability that insulin delivery demand with not change. A label process 722 can annotate or label each detected event with a label to generate a labeled event and annotate or label each classified combination of detected events with a label to generate a labeled event combination. Each labeled event and labeled event combination can be correlated to an insulin demand that will result. Each labeled event or labeled event combination can have either a probability of the increased insulin delivery demand associated with it, a probability of the decreased insulin delivery demand associated with it, or a probability that insulin delivery demand will not change associated with it. To explain further, each labeled event or labeled event combination can be correlated to either: a decreased insulin delivery demand when the probability of the decreased insulin delivery demand is greater than or equal to a first threshold; an increased insulin delivery demand when the probability of the increased insulin delivery demand is greater than or equal to a second threshold; or an ordinary insulin delivery demand when the probability of the decreased insulin delivery demand is less than the first threshold and the probability of the increased insulin delivery demand is less than the second threshold. In this context, "ordinary insulin delivery demand" can refer to an insulin delivery demand that will not change from ordinary levels (e.g., a nominal controller mode in which the controller stays at its nominal mode (most of the day) when there is no change in insulin levels).

In some embodiments, insulin delivery demand can be associated with a predicted glycemic outcome. For instance, in some cases, the insulin delivery demand can be associated with a predicted glycemic outcome that indicates: a probability of an upcoming hyperglycemic condition that would increase insulin delivery demand when the probability is greater than or equal to a threshold, or a probability of an upcoming hypoglycemic condition that would reduce insulin delivery demand when the probability is greater than or equal to another threshold. When a particular labeled event indicates or a particular labeled event combination collectively indicates that the probability of a hypoglycemic condition is more likely to occur or be coming up (e.g., greater than or equal to a threshold), then the controller can switch to a more conservative mode and deliver less insulin. When a particular labeled event indicates or a particular labeled event combination collectively indicates that the probability of a hyperglycemic condition is more to occur or be coming up (e.g., greater than or equal to a threshold), then the controller can switch to a more aggressive mode and deliver more insulin. In other cases, the insulin delivery demand is not associated with a predicted glycemic outcome.

The implementation of the classifier 720 can vary depending on the embodiment. In general terms, the classifier 720 can be implemented using any number of machine learning algorithms and statistical models that will now be described below. Machine learning (ML) algorithms and statistical models can relying on patterns and inference instead of using explicit instructions. Machine learning algorithms build a mathematical model based on sample data, known as "training data," in order to make predictions or decisions without being explicitly programmed to perform the task. For example, supervised learning algorithms build a mathematical model of a set of data that contains both the inputs and the desired outputs. The data is known as training data and consists of a set of training examples. Each training example has one or more inputs and a desired output, also known as a supervisory signal. In the case of semi-supervised learning algorithms, some of the training examples are missing the desired output. In the mathematical model, each training example is represented by an array or vector, and the training data by a matrix. Through iterative optimization of an objective function, supervised learning algorithms learn a function that can be used to predict the output associated with new inputs. An optimal function will allow the algorithm to correctly determine the output for inputs that were not a part of the training data. An algorithm that improves the accuracy of its outputs or predictions over time is said to have learned to perform that task. Supervised learning algorithms include classification and regression. Classification algorithms are used when the outputs are restricted to a limited set of values, and regression algorithms are used when the outputs may have any numerical value within a range. Similarity learning is an area of supervised machine learning closely related to regression and classification, but the goal is to learn from examples using a similarity function that measures how similar or related two objects are.

In predictive modeling and other types of data analytics, ensemble methods can use multiple machine learning algorithms to obtain better predictive performance than could be obtained from any of the constituent learning algorithms alone. An ensemble is a supervised learning algorithm because it can be trained and then used to make predictions. The trained ensemble, therefore, represents a single hypothesis that is not necessarily contained within the hypothesis space of the models from which it is built. Thus, ensembles can be shown to have more flexibility in the functions they can represent. An ensemble model can include a set of individually trained classifiers (such as neural networks or decision trees) whose predictions are combined.

For instance, one common example of ensemble modeling is a random forest model which is a type of analytical model that leverages multiple decision trees and is designed to predict outcomes based on different variables and rules. A random forest model blends decision trees that may analyze different sample data, evaluate different factors or weight common variables differently. The results of the various decision trees are then either converted into a simple average or aggregated through further weighting. The emergence of Hadoop and other big data technologies has allowed greater volumes of data to be stored and analyzed, which can allow analytical models to be run on different data samples.

Depending on the implementation, any number of machine learning models can be combined to optimize the ensemble model. Examples of machine learning algorithms or models that can be implemented at the machine learning model can include, but are not limited to: regression models such as linear regression, logistic regression, and K-means clustering; one or more decision tree models (e.g., a random forest model); one or more support vector machines; one or more artificial neural networks; one or more deep learning networks (e.g., at least one recurrent neural network, sequence to sequence mapping using deep learning, sequence encoding using deep learning, etc.); fuzzy logic based models; genetic programming models; Bayesian networks or other Bayesian techniques, probabilistic machine learning models; Gaussian processing models; Hidden Markov models; time series methods such as Autoregressive Moving Average (ARMA) models, Autoregressive Integrated Moving Average (ARIMA) models, Autoregressive conditional heteroskedasticity (ARCH) models; generalized autoregressive conditional heteroskedasticity (GARCH) models; moving-average (MA) models or other models; and heuristically derived combinations of any of the above, etc. The types of machine learning algorithms differ in their approach, the type of data they input and output, and the type of task or problem that they are intended to solve.

A Hidden Markov model (HMM) is a statistical Markov model in which the system being modeled is assumed to be a Markov process with unobserved (hidden) states. An HMM can be considered as the simplest dynamic Bayesian network. A Bayesian network, belief network or directed acyclic graphical model is a probabilistic graphical model that represents a set of random variables and their conditional independence with a directed acyclic graph (DAG). Bayesian networks that model sequences of variables are called dynamic Bayesian networks. Generalizations of Bayesian networks that can represent and solve decision problems under uncertainty are called influence diagrams.

Support vector machines (SVMs), also known as support vector networks, are a set of related supervised learning methods used for classification and regression. Given a set of training examples, each marked as belonging to one of two categories, an SVM training algorithm builds a model that predicts whether a new example falls into one category or the other. An SVM training algorithm is a non-probabilistic, binary, linear classifier. In addition to performing linear classification, SVMs can efficiently perform a non-linear classification using what is called the kernel trick, implicitly mapping their inputs into high-dimensional feature spaces.

Decision tree learning uses a decision tree as a predictive model to go from observations about an item (represented in the branches) to conclusions about the item's target value (represented in the leaves). Tree models where the target variable can take a discrete set of values are called classification trees; in these tree structures, leaves represent class labels and branches represent conjunctions of features that lead to those class labels. Decision trees where the target variable can take continuous values (typically real numbers) are called regression trees. In decision analysis, a decision tree can be used to visually and explicitly represent decisions and decision making.

Deep learning algorithms can refer to a collection of algorithms used in machine learning, that are used to model high-level abstractions and data through the use of model architectures, which are composed of multiple nonlinear transformations. Deep learning is a specific approach used for building and training neural networks. Deep learning consists of multiple hidden layers in an artificial neural network. Examples of deep learning algorithms can include, for example, Siamese networks, transfer learning, recurrent neural networks (RNNs), long short term memory (LSTM) networks, convolutional neural networks (CNNs), transformers, etc. For instance, deep learning approaches can make use of autoregressive Recurrent Neural Networks (RNN), such as the long short-term memory (LSTM) and the Gated Recurrent Unit (GRU). One neural network architecture for time series forecasting using RNNs (and variants) is an autoregressive seq2seq neural network architecture, which acts as an autoencoder.

In some embodiments, the ensemble model can include one or more deep learning algorithms. It should be noted that any number of different machine learning techniques may also be utilized. Depending on the implementation, the ensemble model can be implemented as a bootstrap aggregating ensemble algorithm (also referred to as a bagging classifier method), as a boosting ensemble algorithm or classifier algorithm, as a stacking ensemble algorithm or classifier algorithm, as bucket of models ensemble algorithms, as Bayes optimal classifier algorithms, as Bayesian parameter averaging algorithms, as Bayesian model combination algorithms, etc.

Bootstrap aggregating, often abbreviated as bagging, involves having each model in the ensemble vote with equal weight. In order to promote model variance, bagging trains each model in the ensemble using a randomly drawn subset of the training set. As an example, the random forest algorithm combines random decision trees with bagging to achieve very high classification accuracy. A bagging classifier or ensemble method creates individuals for its ensemble by training each classifier on a random redistribution of the training set. Each classifier's training set can be generated by randomly drawing, with replacement, N examples—where N is the size of the original training set; many of the original examples may be repeated in the resulting training set while others may be left out. Each individual classifier in the ensemble is generated with a different random sampling of the training set. Bagging is effective on "unstable" learning algorithms (e.g., neural networks and decision trees), where small changes in the training set result in large changes in predictions.

By contrast, boosting involves incrementally building an ensemble by training each new model instance to emphasize the training instances that previous models mis-classified. In some cases, boosting has been shown to yield better accuracy than bagging, but it also tends to be more likely to over-fit the training data. A boosting classifier can refer to a family of methods that can be used to produce a series of classifiers. The training set used for each member of the series is chosen based on the performance of the earlier classifier(s) in the series. In boosting, examples that are incorrectly predicted by previous classifiers in the series are chosen more often than examples that were correctly predicted. Thus, boosting attempts to produce new classifiers that are better able to predict examples for which the current ensemble's performance is poor. A common implementation of boosting is Adaboost, although some newer algorithms are reported to achieve better results.

Stacking (sometimes called stacked generalization) involves training a learning algorithm to combine the predictions of several other learning algorithms. Stacking works in two phases: multiple base classifiers are used to predict the class, and then a new learner is used to combine their predictions with the aim of reducing the generalization error. First, all of the other algorithms are trained using the available data, then a combiner algorithm is trained to make a final prediction using all the predictions of the other algorithms as additional inputs. If an arbitrary combiner algorithm is used, then stacking can theoretically represent any of the ensemble techniques described in this article, although, in practice, a logistic regression model is often used as the combiner.

A "bucket of models" is an ensemble technique in which a model selection algorithm is used to choose the best model for each problem. When tested with only one problem, a bucket of models can produce no better results than the best model in the set, but when evaluated across many problems, it will typically produce much better results, on average, than any model in the set. One common approach used for model-selection is cross-validation selection (sometimes called a "bake-off contest"). Cross-validation selection can be summed up as try them all with the training set and pick the one that works best. Gating is a generalization of Cross-Validation Selection. It involves training another learning model to decide which of the models in the bucket is best-suited to solve the problem. Often, a perceptron is used for the gating model. It can be used to pick the "best" model, or it can be used to give a linear weight to the predictions from each model in the bucket. When a bucket of models is used with a large set of problems, it may be desirable to avoid training some of the models that take a long time to train. Landmark learning is a meta-learning approach that seeks to solve this problem. It involves training only the fast (but imprecise) algorithms in the bucket, and then using the performance of these algorithms to help determine which slow (but accurate) algorithm is most likely to do best.

The Bayes optimal classifier is a classification technique. It is an ensemble of all the hypotheses in the hypothesis space. On average, no other ensemble can outperform it. The naive Bayes optimal classifier is a version of this that assumes that the data is conditionally independent on the class and makes the computation more feasible. Each hypothesis is given a vote proportional to the likelihood that the training dataset would be sampled from a system if that hypothesis were true. To facilitate training data of finite size, the vote of each hypothesis is also multiplied by the prior probability of that hypothesis. The hypothesis represented by the Bayes optimal classifier, however, is the optimal hypothesis in ensemble space (the space of all possible ensembles.

Bayesian parameter averaging (BPA) is an ensemble technique that seeks to approximate the Bayes optimal classifier by sampling hypotheses from the hypothesis space and combining them using Bayes' law. Unlike the Bayes optimal classifier, Bayesian model averaging (BMA) can be practically implemented. Hypotheses are typically sampled using a Monte Carlo sampling technique such as MCMC. For example, Gibbs sampling may be used to draw hypotheses that are representative of a distribution. It has been shown that under certain circumstances, when hypotheses are drawn in this manner and averaged according to Bayes' law, this technique has an expected error that is bounded to be at most twice the expected error of the Bayes optimal classifier.

Bayesian model combination (BMC) is an algorithmic correction to Bayesian model averaging (BMA). Instead of sampling each model in the ensemble individually, it samples from the space of possible ensembles (with model weightings drawn randomly from a Dirichlet distribution having uniform parameters). This modification overcomes the tendency of BMA to converge toward giving all of the weight to a single model. Although BMC is somewhat more computationally expensive than BMA, it tends to yield dramatically better results. The results from BMC have been shown to be better on average (with statistical significance) than BMA, and bagging. The use of Bayes' law to compute model weights necessitates computing the probability of the data given each model. Typically, none of the models in the ensemble are exactly the distribution from which the training data were generated, so all of them correctly receive a value close to zero for this term. This would work well if the ensemble were big enough to sample the entire model-space, but such is rarely possible. Consequently, each pattern in the training data will cause the ensemble weight to shift toward the model in the ensemble that is closest to the distribution of the training data. It essentially reduces to an unnecessarily complex method for doing model selection. The possible weightings for an ensemble can be visualized as lying on a simplex. At each vertex of the simplex, all of the weight is given to a single model in the ensemble. BMA converges toward the vertex that is closest to the distribution of the training data. By contrast, BMC converges toward the point where this distribution projects onto the simplex. In other words, instead of selecting the one model that is closest to the generating distribution, it seeks the combination of models that is closest to the generating distribution. The results from BMA can often be approximated by using cross-validation to select the best model from a bucket of models. Likewise, the results from BMC may be approximated by using cross-validation to select the best ensemble combination from a random sampling of possible weightings.

Referring again to FIG. 10, each labeled event and each labeled event combination can be stored in storage 728 as a database of labeled events and labeled event combinations. Selected ones of the labeled events and/or selected ones of the labeled event combinations can be processed at a client application 740 to generate an output result. The client application 740 can vary depending on the implementation, and can include any number of different client applications. In the context of insulin therapy management, non-limiting examples of client applications that can be improved or optimized by enriching the input data (e.g., using selected ones of the labeled events and/or labeled event combinations) can include, but are not limited to: a mathematical model that represents the physiology of a user, a controller for an insulin infusion device, a healthcare management application (e.g., for insulin therapy management), an application for calibrating an insulin therapy system of a user, etc.

When the client application 740 is a controller for an insulin infusion device 702, selected ones of the labeled events and/or labeled event combinations can be processed at the controller to generate one or more therapy parameters for controlling delivery of insulin via the insulin infusion device 702. Non-limiting examples of therapy parameters can include a basal profile, an active insulin time, an insulin sensitivity factor of the user, an insulin-to-carbohydrate ratio for the user, a total daily dose (TDD) of insulin delivered to the user, and the like. The controller can then generate, based on the one or more therapy parameters, recommended settings or commands to control delivery of insulin via the insulin infusion device 702.

Non-limiting examples of therapy parameters can include a basal profile, an active insulin time, an insulin sensitivity factor of the user, an insulin-to-carbohydrate ratio for the user, and a total daily dose of insulin delivered to the user.

As used herein, the term "basal insulin" can refer to a therapy setting for an insulin infusion device that specifies an hourly, continuous infusion of insulin delivered automatically by an insulin infusion device based on preprogrammed profiles and personalized rates set in the insulin infusion device. The insulin infusion device delivers a daily infusion of insulin that typically covers "background" insulin needs during periods of fasting (e.g., overnight and between meals). The basal profile can include at least one basal rate setting for the user that indicates a rate of continuous insulin infusion delivered to the user to keep blood glucose of the user stable during fasting periods. As used herein, the term "basal rate" can refer to a therapy setting for an insulin infusion device that provides a delivery rate that indicates a continuous infusion of insulin to keep blood glucose stable, for example, between meals and during the night for a specific patient. Basal insulin mimics pancreatic insulin delivery, which meets all the body's non-food related insulin needs. A basal rate profile can define a plurality of basal rates corresponding to a plurality of time segments (e.g., during a 24-hour day). As used herein, the term "a maximum basal rate" can refer to a therapy setting for an insulin infusion device that specifies a maximum amount of basal insulin that an insulin infusion device should deliver at one time for a specific patient.

As used herein, the term "active insulin" or "insulin on board (IOB)" can refer to bolus insulin that has been delivered to a user's body, but that has not yet been used by the patient. For example, active insulin can refer to how much insulin is still active inside the body from the previous bolus dose. Stated differently, the active insulin time can indicate an amount of time a bolus of insulin remains active in a user after injection. As used herein, the term "active insulin time" can refer to a therapy setting for an insulin infusion device that specifies a duration of insulin action in a specific user's body, or an amount of time insulin remains working in a specific user's body after a bolus of rapid acting insulin. Active insulin time (sometime also referred to as duration of insulin action (DIA)) can refer to how long a bolus of insulin takes to be absorbed by a user's body and finish lowering blood glucose. The time starts when a bolus is given and ends when the bolus is no longer lowering blood glucose levels. An accurate active insulin time can help minimize insulin stacking and low blood sugar (hypoglycemia), which can happen when boluses are given too close together. Active insulin time varies from person to person. As used herein, the term "a maximum bolus limit" can refer to a therapy setting for an insulin infusion device that specifies a maximum amount of bolus insulin that an insulin infusion device should deliver at one time for a specific patient.

As used herein, the term "insulin sensitivity factor (ISF)" or "correction factor" can refer to a therapy setting for an insulin infusion device that specifies an amount that a specific user's blood glucose (BG) level (e.g., in mg/dL or mmol/L) is reduced by one unit of insulin. In other words, ISF can indicate how much one unit of insulin is expected to lower blood sugar, and can describe the amount of bolus that is delivered per 1 mg/dL deviation of glucose from a target glucose value.

As used herein, the term "insulin-to-carbohydrate ratio" can refer to a therapy setting for an insulin infusion device that specifies an amount of insulin required to cover a given number of carbohydrates. For instance, the insulin-to-carbohydrate ratio can indicate an amount of bolus insulin that is delivered per one unit of carbohydrate intake. In other words, insulin-to-carbohydrate ratio can refer to the number of grams of carbohydrates "covered" by one unit of insulin. By contrast, the carbohydrate-to-insulin ratio for a user indicates a ratio of an amount of carbohydrates in grams covered by one unit of insulin.

As used herein, the term "total daily dose (TDD)" can refer to a number on insulin units that a user of an insulin infusion device uses (e.g., on average) per day. The total daily dose of insulin can be computed based on the total basal insulin delivered to the user and total bolus insulin delivered to the user. As used herein, the term "bolus insulin" can refer to a therapy setting for an insulin infusion device that specifies a dose of insulin for a specific patient that is needed to cover an expected rise in blood glucose (such as the rise after a meal or a snack) or to lower a high blood glucose down to target range. Target blood glucose or "target range" is a setting that indicates a desired blood glucose level. It can be entered into an insulin infusion device as a single target for the entire day (e.g., 120 mg/dl) or as a range (e.g., 100-120 mg/dl). Many insulin infusion devices have a built-in bolus calculator that calculates how much insulin to take for a meal or for correcting blood sugars. Bolus calculator settings can include: target blood glucose/range; insulin-to-carbohydrate ratio (I:C) or carbohydrate-to-insulin (C:I) ratio; insulin sensitivity factor (ISF) or correction factor; active insulin time or duration of insulin action (DIA), and insulin on board (IOB).

For example, the total daily dose may be computed using insulin delivery data, including basal insulin and insulin bolus amounts, along with their associated time data (time/date stamps). The total daily dose can be used to compute the patient's insulin sensitivity factor (ISF), which is expressed in mg/dL/Unit, and/or insulin-to-carbohydrate ratio (I:C).

When the client application 740 is a mathematical model that represents the physiology of a user, the mathematical model can be trained based on selected ones of the labeled events and/or labeled event combinations to generate an adapted mathematical model that simulates a physiological blood glucose response of the user in response to the selected ones of the labeled events and/or labeled event combinations.

When the client application 740 is a healthcare management application (HMA) for insulin therapy management, the HMA can track events associated with the user that are indicative of physical behavior of the user and correspond to selected ones of the labeled events and/or to selected ones of the labeled event combinations. The HMA can then generate one or more user interfaces that provide information indicating an impact of one or more of the tracked events on blood glucose levels of the user and insulin demand of the user.

When the client application 740 is an application for calibrating an insulin therapy system of the user, selected ones of the labeled events and/or to selected ones of the labeled event combinations can be processed to calibrate the insulin therapy system of the user. Calibration can include, for example, generating recommended therapy settings and parameters for calibrating the insulin therapy system of the user.

Figure 11:
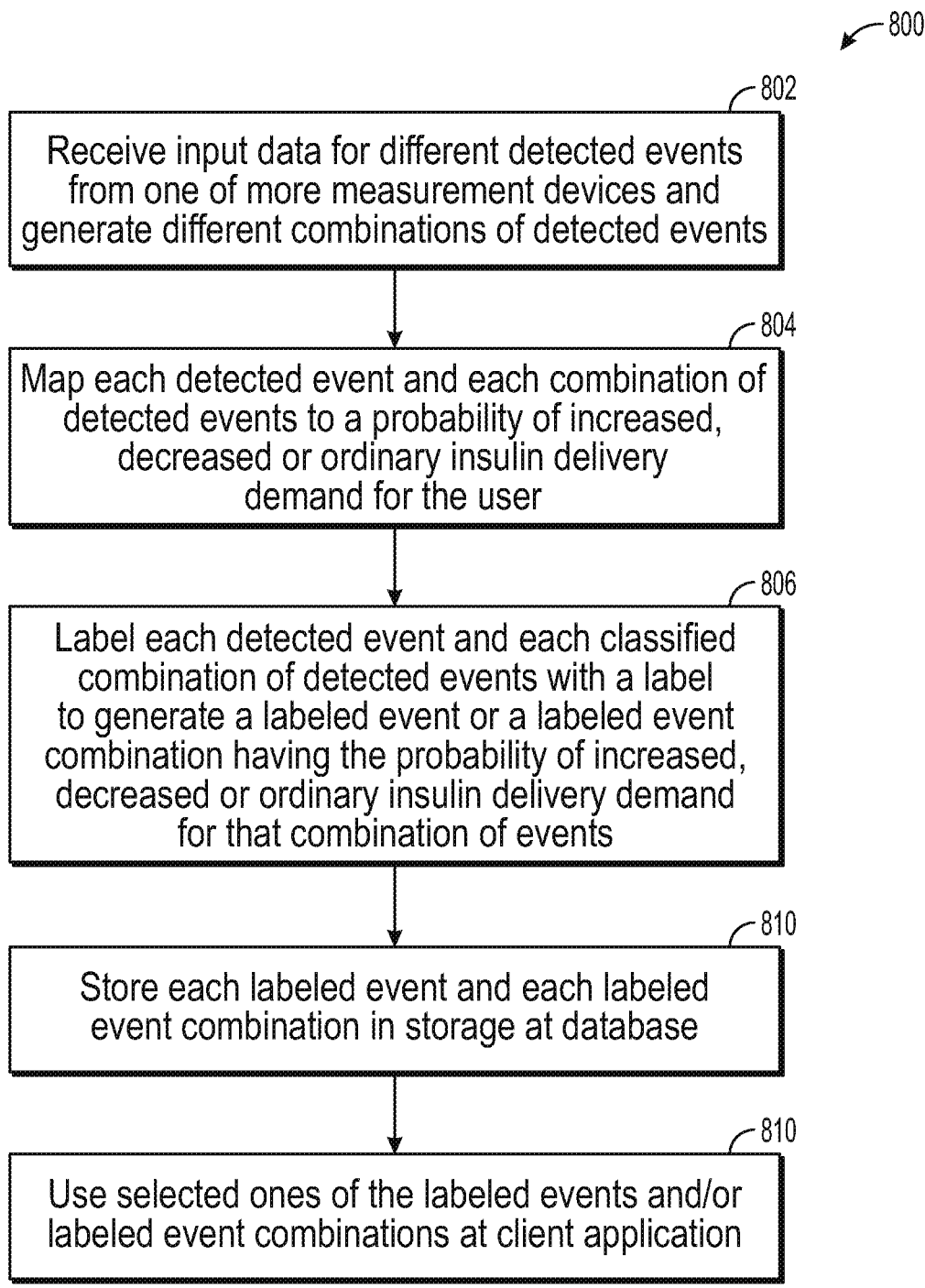
FIG. 11 is a flowchart illustrating a method for classifying detected events for processing at a client application in accordance with certain embodiments.

FIG. 11 is a flowchart illustrating a method 800 for classifying detected events for processing at a client application 740 in accordance with certain embodiments. The method 800 starts at 802, where a server system 716 receives input data for detected events and different combinations of detected events. In one non-limiting embodiment, the input data for detected events can include data regarding a specific condition or physical activity that is indicative of a physical behavior of the user. The specific conditions or activities that are indicative of the physical behavior of the user can include, but are not limited to, any of the examples described with reference to FIG. 10.

The method 800 continues at 804, where each detected event and combination of detected events is processed at the server system 716. At 804, an event classifier 720 can classify each detected event and each combination of detected events by mapping that detected event or combination of detected events to a probability of an increased insulin delivery demand, a probability of a decreased insulin delivery demand, or a probability that insulin delivery demand with not change.

At 806, each classified event and each classified combination of detected events that results can be annotated or labeled with a label to generate a labeled event that is correlated to an insulin demand that will result or a labeled event combination that is correlated to an insulin demand that will result. Each labeled event and each labeled event combination can have either a probability of the increased insulin delivery demand associated with it, a probability of the decreased insulin delivery demand associated with it, or a probability that insulin delivery demand with not change associated with it. As explained above, each labeled event and each labeled event combination can be correlated to either: a decreased insulin delivery demand when the probability of the decreased insulin delivery demand is greater than a first threshold; an increased insulin delivery demand when the probability of the increased insulin delivery demand is greater than a second threshold; or an ordinary insulin delivery demand when the probability of the decreased insulin delivery demand is less than the first threshold and the probability of the increased insulin delivery demand is less than the second threshold.

At 810, each labeled event and each labeled event combination can be stored in storage 728 as a database of labeled events and labeled event combinations. At 812, selected ones of the labeled events and/or selected ones of the labeled event combinations can be processed at a client application 740 to generate an output result. The client application 740 can vary depending on the implementation, as described with reference to FIG. 10.

As noted above with reference to FIG. 10, in one embodiment, the client application 740 can be a mathematical model that represents the physiology of a user. The mathematical model can be trained based on selected ones of the labeled events and/or labeled event combinations to generate an adapted mathematical model that simulates a physiological blood glucose response of the user in response to the selected ones of the labeled events and/or labeled event combinations. An example embodiment will now be described with reference to FIGS. 12-14.

Figure 12:
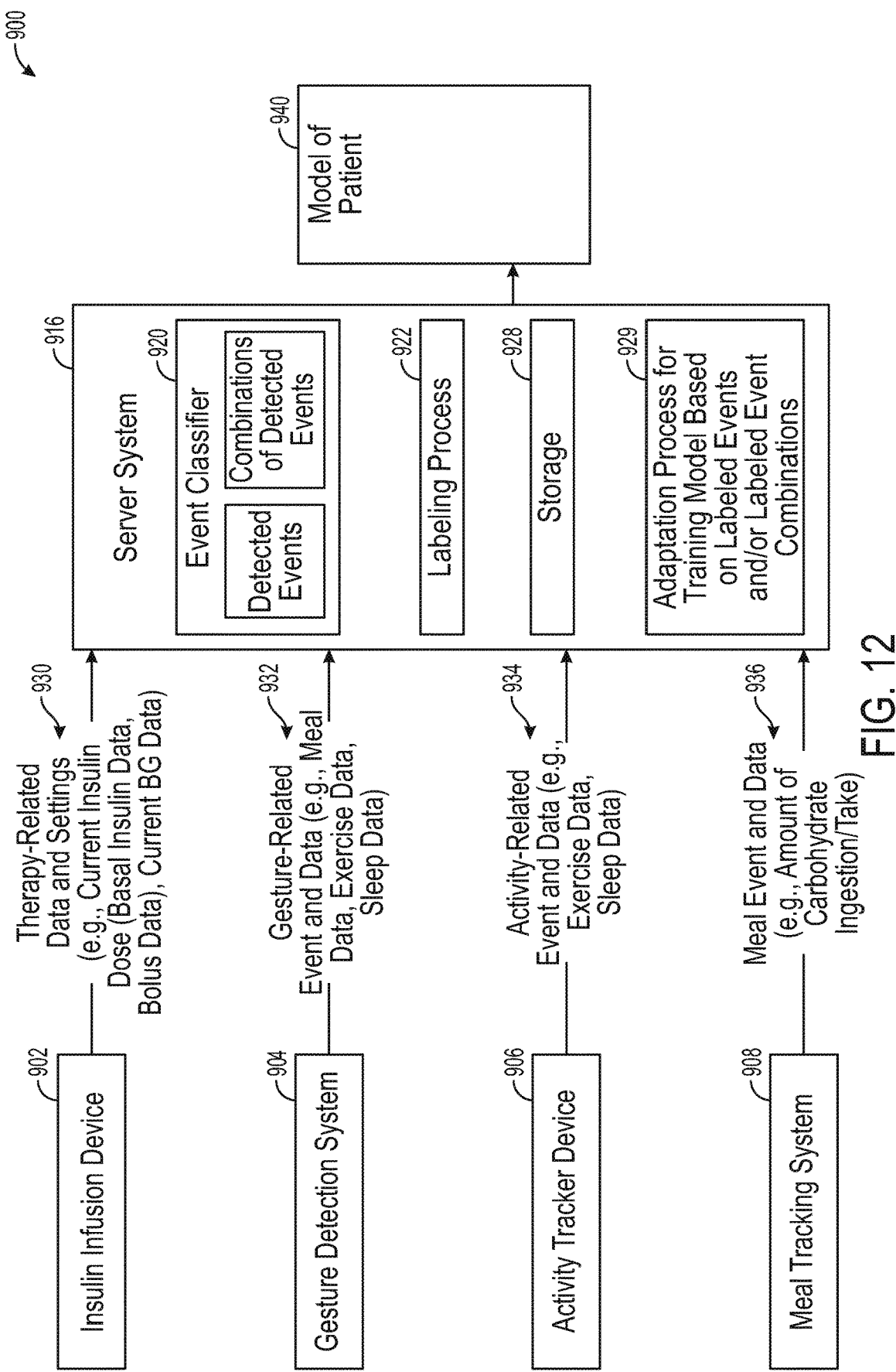
FIG. 12 is a block diagram illustrating a system for training a mathematical model in accordance with certain embodiments.

FIG. 12 is a block diagram illustrating a system 900 in accordance with certain embodiments. As in FIG. 10, in one non-limiting implementation, the system 900 can include an insulin infusion device 902 of a user, a gesture detection system 904, a gesture detection device 906, a meal tracking system 908, and a server system 916. These devices and systems are described with reference to FIG. 10, and for sake of brevity, the description of these devices and systems will not be repeated. As described with reference to FIG. 10, although not illustrated, the system 900 can also include other systems and components that can be part of the event detection system 107 of FIG. 1, the gesture-based event detection system 500 of FIG. 8, and the gesture-informed patient management system 600 of FIG. 9. As in FIG. 10, the gesture detection system 904, the activity tracker device 906, and the meal tracking system 908 are non-limiting examples of the systems and devices that can be part of the event detection system 107 of FIG. 1. The system 900 can also include a personal user device (e.g., smart phone or computer) for entering carbohydrate intake and/or blood glucose levels. The system can also optionally include other components, such as a blood glucose meter.

The server system 916 (having an event classifier 920, a labeling process 922, and storage 928) can be implemented using any of the event classification service 111, the database 114 and the data processing system 116 described with respect to FIG. 1, the server system 716 described with respect to FIG. 10. These devices, systems and models are described with reference to FIGS. 1-11, and for sake of brevity, the description of these devices, systems and models will not be repeated. The system 900 of FIG. 12 differs from system 700 of FIG. 10 in that in this embodiment, the server system 916 includes an adaptation process 929 and the client application is a mathematical model 940. Depending on the implementation, the mathematical model 940 can be implemented at the server system 916 or at another computer-based system that is distinct from the server system 916. The system 900 can be used to classify events detected by the insulin infusion device 902, the gesture detection system 904, the activity tracker device 906, and/or the meal tracking system 908 as labeled events and/or labeled event combinations. Some or all of these labeled events and/or labeled event combinations can be processed at the mathematical model 940 to train it and generate an adapted mathematical model of the user. The implementation of mathematical model 940 can vary depending on the embodiment. For example, the mathematical model 940 can be implemented using various equations that will be described below with reference to FIG. 14. Alternatively, the mathematical model 940 can be implemented using any number of machine learning algorithms and/or statistical models that are described with respect to the classifier 720 of FIG. 10. For sake of brevity a description of those models will not be repeated with respect to mathematical model 940.

The server system 916 receives input data for different detected events. As described with reference to FIG. 10, the detected events can be stored and processed at the server system 716. The server system 716 can group the detected events into different combinations of detected events. The detected events and different combinations of detected events can then be further processed at an event classifier 920 and labeling process 922 as described with reference to FIG. 10, and then stored as a database of labeled events and labeled event combinations at storage 928. As described with reference to FIG. 10, each labeled event and each labeled event combination can include a label and a probability of an increased insulin delivery demand or a decreased insulin delivery demand for that particular labeled event or that particular labeled event combination. For example, each labeled event and labeled event combination can be correlated to a decreased insulin delivery demand when the probability of the decreased insulin delivery demand is greater than a first threshold; an increased insulin delivery demand when the probability of the increased insulin delivery demand is greater than a second threshold; or an ordinary insulin delivery demand when the probability of the decreased insulin delivery demand is less than the first threshold and the probability of the increased insulin delivery demand is less than the second threshold. In some cases, the insulin delivery demand can be associated with a predicted glycemic outcome that indicates: a probability of an upcoming hyperglycemic condition that would increase insulin delivery demand when the probability is greater than a threshold, or a probability of an upcoming hypoglycemic condition that would reduce insulin delivery demand when the probability is greater than another threshold.

The adaptation process 929 (e.g., implemented at a server system 916) can retrieve selected ones of the labeled events and/or the labeled event combinations from a database maintained in storage 928. The labeled events and/or the labeled event combinations can vary depending on the implementation and the training that is being done. The labeled events and/or the labeled event combinations that were selected and retrieved by the adaptation process 929 can be used to train the mathematical model 940 of a user to generate an adapted mathematical model of the user.

In one embodiment, the mathematical model 940 represents the physiology of the user, and the mathematical model can be trained to generate an adapted mathematical model of the user that simulates a physiological blood glucose response of the user in response to the selected ones of the labeled events and/or labeled event combinations. For instance, in one embodiment, one or more parameters of equations of the mathematical model 940 can be defined based on the selected ones of the labeled events and/or the labeled event combinations to generate the adapted mathematical model of the user that simulates a physiological blood glucose response of the user in response to the selected ones of the detected events and the labeled event combinations. Each parameter that is defined is modifiable as a function of one or more of the selected ones of the labeled events and/or the labeled event combinations.

In one embodiment, the mathematical model 940 can be a "digital twin" of a specific user or patient. The digital twin can be cloud-based, or in cases where the infusion device has robust and powerful processing capabilities, the creation, updating, and management of the digital twin need not be implemented in the cloud, but can instead be implemented at the infusion device itself. Examples embodiments of a digital twin may be of the type described in, but not limited to, United States Patent Publication No. US-2019-0321553-A1 and U.S. patent application Ser. No. 16/438,407, each of which are incorporated by reference herein in their entirety.

The digital twin can be a mathematical model or simulation of a user or "virtual patient." For example, a digital twin can be implemented using a set of differential equations derived from the patient's historical data that together define or describe the patient's blood glucose response to carbohydrate intake and insulin delivery. In this regard, the resulting patient-specific model used for the digital twin represents the model that best fits the patient's historical sensor glucose measurement data for the period of time under evaluation used to generate the model.

The "output" of the digital twin is a predicted blood glucose level or profile of a user based on "inputs" that are likely to influence the patient's glycemic state, such as an amount of insulin delivered to a user (e.g., patient), an amount of carbohydrate consumed by the user, and/or the like, in conjunction with the various patient-specific parameter values associated with the model. In other words, the digital twin can have various parameters, and the values of the parameters are unique to each individual user or patient. For example, each digital twin may be personalized and compute a patient-specific set of values for various closed-loop control parameters (e.g., PID gain coefficient values, PID time constants, basal insulin delivery rates, carbohydrate ratios, insulin sensitivity factors, target glucose values, and the like), which may be unique to each individual patient. Examples of such parameters will be described below with reference to FIG. 14.

The digital twin can be utilized in various ways to enhance, improve, or optimize the manner in which the user's insulin infusion device regulates and controls the insulin therapy. For example, the digital twin can be used to determine how best to adjust the parameters of the insulin delivery control algorithm(s) used by an insulin delivery controller of the user's insulin infusion device. The digital twin can be used to optimally and automatically set all relevant settings, gains, and parameters of an insulin infusion device in a way that is personalized to a specific user. For instance, the digital twin can compute therapy-related data such as a basal profile including basal rates, insulin to carbohydrate (I:C) ratios, an insulin sensitivity factor (ISF), insulin feedback gains (IFB), gains that are applied to a PID controller, model predictive gains, etc. to improve insulin pump therapy on an individualized basis. Recommended adjustments can be implemented by the insulin delivery controller automatically, or they can be made after confirmation by the patient, a caregiver, a parent, etc.

Figure 13:
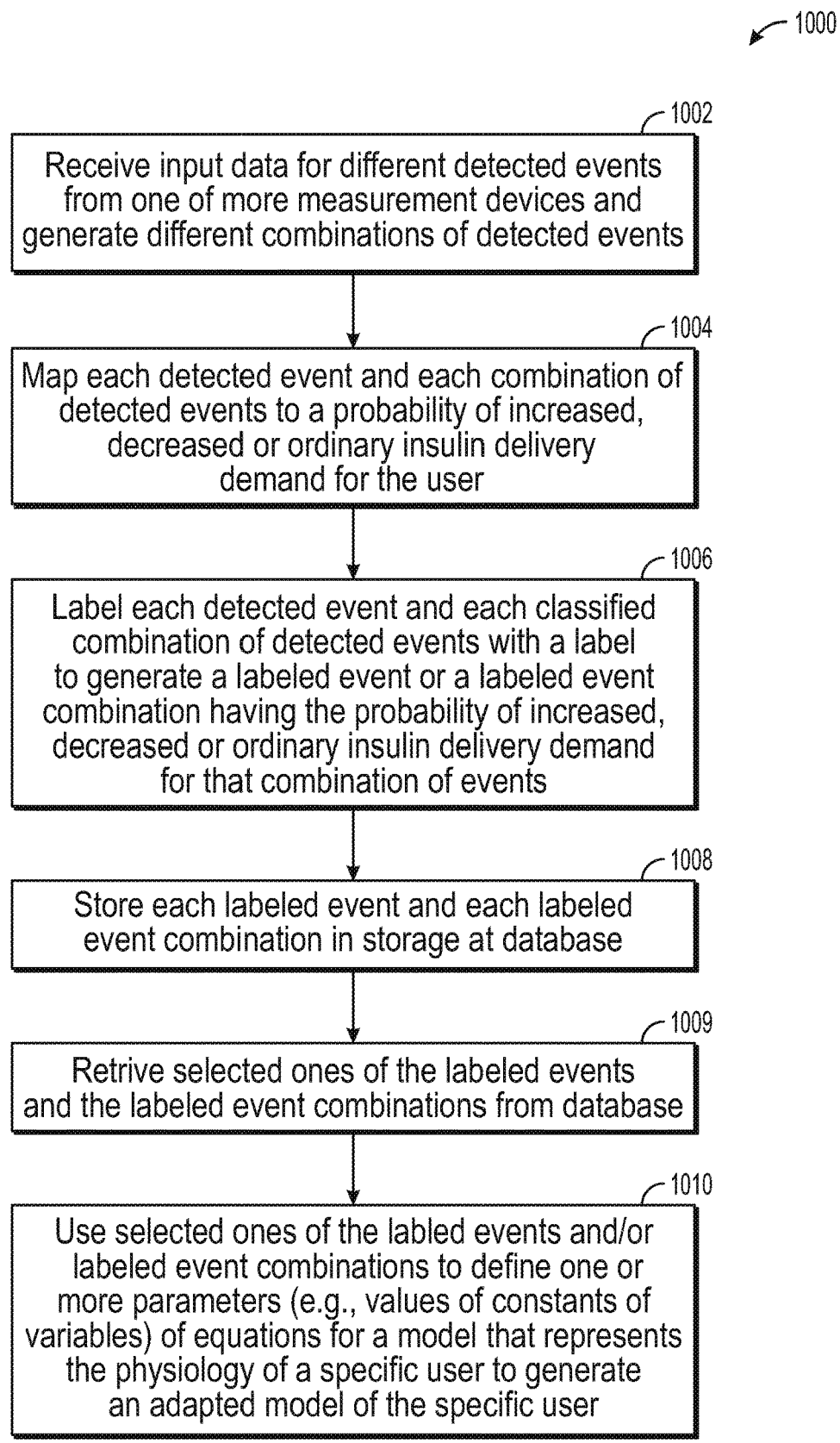
FIG. 13 is a flowchart illustrating a method for training a mathematical model based on labeled events and/or labeled event combinations in accordance with certain embodiments.

FIG. 13 is a flowchart illustrating a method 1000 for training a mathematical model 940 based on labeled events and/or labeled event combinations in accordance with certain embodiments. Steps 1002, 1004, 1006 and 1008 of FIG. 13 are identical to steps 802, 804, 806 and 808 of FIG. 11, and therefore, for sake of brevity, will not be repeated here again. As described with reference to FIG. 10, storage 928 (FIG. 12) stores a database of detected events as labeled events and different combinations of the detected events as labeled event combinations. Each labeled event and each labeled event combination can include a label and a probability of an increased insulin delivery demand or a decreased insulin delivery demand for that particular labeled event or that particular labeled event combination. For example, each labeled event and labeled event combination can be correlated to a decreased insulin delivery demand when the probability of the decreased insulin delivery demand is greater than a first threshold; an increased insulin delivery demand when the probability of the increased insulin delivery demand is greater than a second threshold; or an ordinary insulin delivery demand when the probability of the decreased insulin delivery demand is less than the first threshold and the probability of the increased insulin delivery demand is less than the second threshold. In some cases, the insulin delivery demand can be associated with a predicted glycemic outcome that indicates: a probability of an upcoming hyperglycemic condition that would increase insulin delivery demand when the probability is greater than a threshold, or a probability of an upcoming hypoglycemic condition that would reduce insulin delivery demand when the probability is greater than another threshold.

Method 1000 of FIG. 13 differs from method 800 of FIG. 11 as follows. At 1009, an adaptation process 929 at a server system 916 can retrieve selected ones of the labeled events and/or the labeled event combinations from a database maintained in storage 928. The labeled events and/or the labeled event combinations can vary depending on the implementation and the training that is being done.

At 1010, the labeled events and/or the labeled event combinations that were selected and retrieved (at 1009) can be used to train a mathematical model 940 that represents the physiology of a user to generate an adapted mathematical model of the user. For example, the mathematical model can be trained to generate an adapted mathematical model of the user that simulates a physiological blood glucose response of the user in response to the selected ones of the labeled events and/or labeled event combinations. For instance, in one embodiment, one or more parameters of equations of the mathematical model 940 can be defined based on the selected ones of the labeled events and/or the labeled event combinations to generate the adapted mathematical model of the user that simulates a physiological blood glucose response of the user in response to the selected ones of the detected events and the labeled event combinations. Each parameter that is defined is modifiable as a function of one or more of the selected ones of the labeled events and/or the labeled event combinations.

FIG. 14 is a table (TABLE 1) that shows examples of adjustable therapy parameters and whether they are impacted by a detected event (as designated by the symbol X) or not impacted by the detected event (as designated by the symbol N/A).

In this non-limiting example shown in TABLE 1, the adjustable parameters show various constants and parameters that can be impacted and modified in response to a detected event. The adjustable parameters include: a first patient-specific time constant ($\tau_1$) (minutes) that represents the net insulin diffusion rate between the subcutaneous compartment and the plasma compartment; a second patient-specific time constant ($\tau_2$) (minutes) that represents a rate of insulin removal; a third patient-specific time constant ($\tau_3$) (minute) that represents the net glucose diffusion rate between the subcutaneous compartment and the plasma compartment; a fourth patient-specific time constant ($\tau_4$): (minutes) that represents a rate of glucose removal; a fifth patient-specific time constant ($\tau_5$) (minutes) that represents a net glucose diffusion rate between the digestion compartments and the plasma compartment; a patient-specific meal absorption constant ($K_M$) (mg/CARB) that represents a stochiometric conversion of the carbohydrates (CARB) from meal ingestion into glucose concentration; and an insulin utilization of glucose parameter ($K_1$): (mg/(U minute)) that represents insulin utilization of glucose. In this example, the detected events include: physical activity, meal ingestion, sleep, sickness, which may be related to heart rate with body temperature, and stress, which may be related to heart rate with body temperature.

As illustrated in Table 1 of FIG. 14, the first patient-specific time constant ($\tau_1$) (minutes) that represents the net insulin diffusion rate between the subcutaneous compartment and the plasma compartment can be impacted by all of the detected events except meal ingestion; the second patient-specific time constant ($\tau_2$) (minutes) that represents the rate of insulin removal can be impacted by all of the detected events except meal ingestion; the third patient-specific time constant ($\tau_3$) (minute) that represents the net glucose diffusion rate between the subcutaneous compartment and the plasma compartment can be impacted by all of the detected events except meal ingestion; a fourth patient-specific time constant ($\tau_4$): (minutes) that represents a rate of glucose removal; the fifth patient-specific time constant ($\tau_5$) (minutes) that represents the net glucose diffusion rate between the digestion compartments and the plasma compartment can be impacted by all of the detected events except sleep; the patient-specific meal absorption constant ($K_M$) (mg/CARB) that represents the stochiometric conversion of the carbohydrates (CARB) from meal ingestion into glucose concentration can be impacted by all of the detected events except sleep; and the insulin utilization of glucose parameter ($K_1$): (mg/(U minute)) that represents insulin utilization of glucose can be impacted by all of the detected events except meal ingestion.

It should be appreciated that the examples of adjustable therapy parameters and detected events shown in TABLE 1 are non-limiting and provided for illustrative purposes. In this regard, is should be noted that the adjustable therapy parameters that are shown in TABLE 1 can be modifiable based on other detected events that are not shown in TABLE 1, and that other adjustable therapy parameters that are not shown in TABLE 1 can be modifiable based on detected events that are shown in TABLE 1 and/or other detected events detected events that are not shown in TABLE 1.

As described with reference to FIG. 12-14, a mathematical model that represents the physiology of a user can be trained based on selected ones of the labeled events and/or labeled event combinations to generate an adapted mathematical model that simulates a physiological blood glucose response of the user in response to the selected ones of the labeled events and/or labeled event combinations. An alternative embodiment will now be described with reference to FIGS. 15-17.

Figure 15:
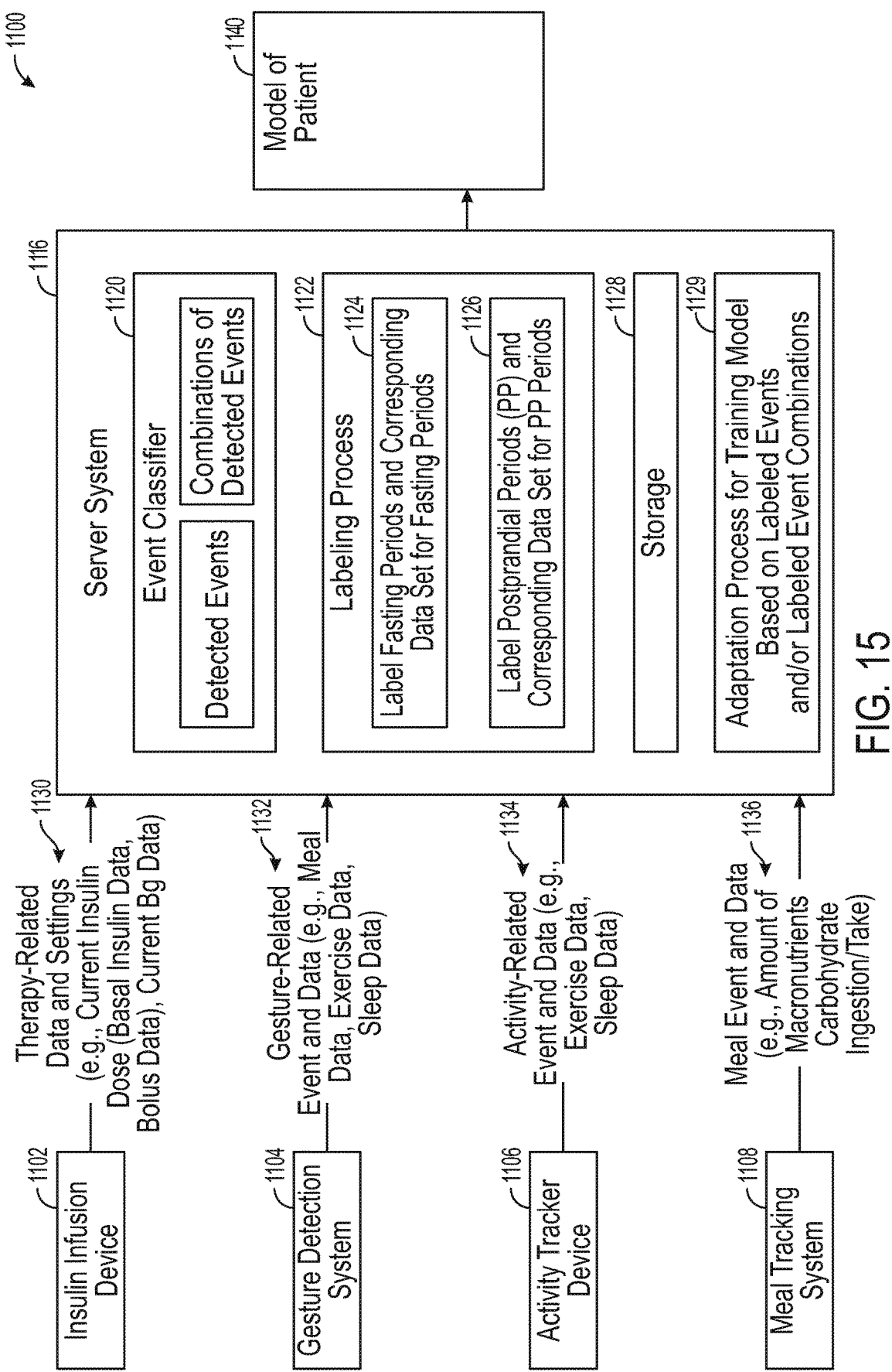
FIG. 15 is a block diagram illustrating another system for training a mathematical model in accordance with certain embodiments.

FIG. 15 is a block diagram illustrating a system 1100 in accordance with certain embodiments. As in FIG. 12, in one non-limiting implementation, the system 1100 can include an insulin infusion device 1102 of a user, a gesture detection system 1104, a gesture detection device 1106, a meal tracking system 1108, a server system 1116 (having an event classifier 1120, a labeling process 1122, and storage 1128), and a mathematical model 1140. These devices, systems and models are described with reference to FIGS. 10-13, and for sake of brevity, the description of these devices, systems and models will not be repeated. As described with reference to FIG. 10, although not illustrated, the system 1100 can also include other systems and components that can be part of the event detection system 107 of FIG. 1. As such, the gesture detection system 1104, the activity tracker device 1106, and the meal tracking system 1108 are non-limiting examples of the systems and devices that can be part of the event detection system 107 of FIG. 1.

The system 1100 of FIG. 15 differs from system 700 of FIG. 12 in that the labeling process 1122 can perform further processing of detected events and/or combinations thereof to determine fasting periods and a corresponding data set for fasting periods and to determine postprandial periods and a corresponding data set of postprandial periods. In addition, the adaptation process 1129 can retrieve selected ones of the labeled events and/or the labeled event combinations for different periods from the database maintained in storage 1128 and generate different streams of the labeled events and/or labeled event combinations for the different periods that are used to train different aspects of the mathematical model 1140.

For example, the adaptation process 1129 can retrieve selected ones of the labeled events and/or the labeled event combinations for fasting periods from the database maintained in storage 1128 and generate one or more streams of the labeled events and/or labeled event combinations for fasting periods that are used to train certain aspects of the mathematical model 1140. In one embodiment, certain parameters of equations of the mathematical model 1140 can be defined for fasting periods, based on the selected ones of the labeled events and/or the labeled event combinations for fasting periods, to generate an adapted mathematical model of the user during fasting periods. That adapted mathematical model identifies fasting parameters of the physiological blood glucose response of the user in response to those selected ones of the labeled events and/or the labeled event combinations during fasting periods. Those parameters that are defined are modifiable as a function of one or more of the selected ones of the labeled events and/or the labeled event combinations for the fasting periods.

By contrast, the adaptation process 1129 can retrieve other selected ones of the labeled events and/or the labeled event combinations for postprandial periods from the database maintained in storage 1128 and generate a separate stream of the labeled events and/or labeled event combinations for postprandial periods that are used to train other aspects of the mathematical model 1140. In one embodiment, other parameters of equations of the mathematical model 1140 can be defined for postprandial periods, based on the selected ones of the labeled events and/or the labeled event combinations for postprandial periods, to generate an adapted mathematical model of the user during postprandial periods. That adapted mathematical model identifies fasting parameters of a physiological blood glucose response of the user in response to those selected ones of the labeled events and/or the labeled event combinations during postprandial periods. Those parameters that are defined are modifiable as a function of one or more of the selected ones of the labeled events and/or the labeled event combinations for the postprandial periods.

Figure 16:
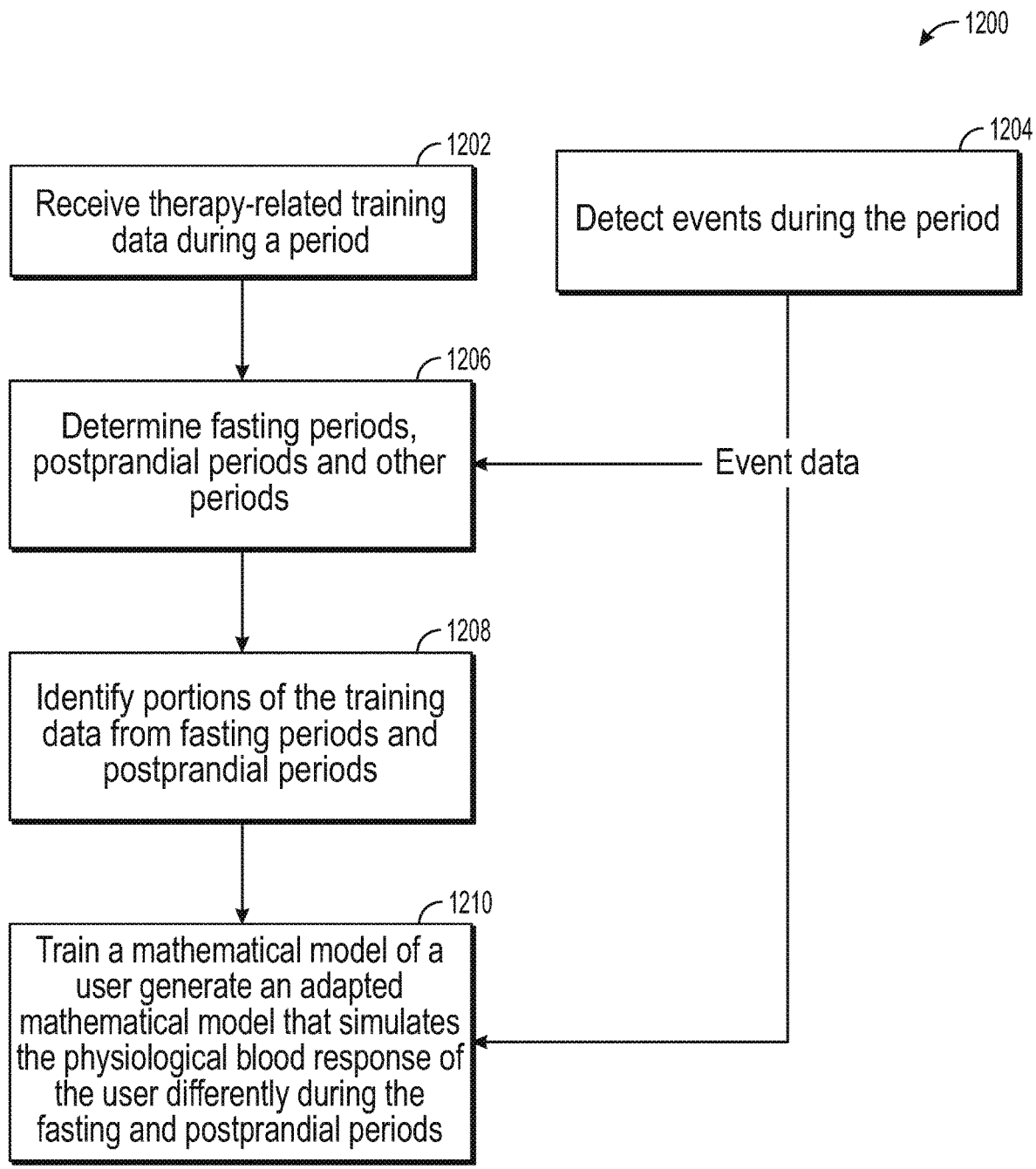
FIG. 16 is a flowchart illustrating a method for training a mathematical model based on labeled events and/or labeled event combinations in accordance with certain embodiments.

FIG. 16 is a flowchart illustrating a method 1000 for training a mathematical model 1140 based on labeled events and/or labeled event combinations in accordance with certain embodiments.

At 1202, the server system 1116 can receive one or more streams of training data during a period. The training data can include therapy-related data and settings from an insulin infusion device of a user. In one embodiment, the therapy-related data and settings describe one or more of: blood glucose levels of a user during the period and insulin delivery to the user during the period.

At 1204, an event detection system can detect events during the period. Each detected event can be a specific condition or physical activity that is indicative of a physical behavior of the user, such as, meal ingestion events; sleep events; physical activity events; exercise events; work-related events, etc.

At 1206, a labeling process 1122 can process the training data and the detected events to determine timing of fasting periods within one or more streams of training data, postprandial periods within one or more streams of training data, and timing of other periods within one or more streams of training data that are inconclusive (e.g., not indicative of fasting or postprandial periods). The fasting periods can be periods that are determined to be sufficiently accurate to be indicative of a fasting glucose condition. The postprandial periods can be periods that are determined to be sufficiently accurate to be indicative of a non-fasting glucose condition that occurs when user has consumed food during the period.

At 1208, the labeling process 1122 can identify parts of the training data from the fasting periods within one or more streams of training data and other parts of the training data from the postprandial periods within one or more streams of training data.

At 1210, the adaptation process 1129 can train a mathematical model of a user to generate an adapted mathematical model based on the parts of the training data for the fasting periods and based on the other parts of the training data from the postprandial periods. The adaptation process 1129 can train the mathematical model of the user based on the training data for the fasting periods to adapt the mathematical model of the user to identify fasting parameters of a physiological blood glucose response of the user, and can train the mathematical model of the user based on the other training data from the postprandial periods to further adapt the mathematical model of the user to identify fasting parameters of a physiological blood glucose response of the user differently during postprandial periods. In some implementations, the adaptation process 1129 can train the mathematical model in different iterations, for example, first based on the training data for the fasting periods, and then based on the other training data from the postprandial periods, or vice-versa. Alternatively or additionally, in some implementations, the adaptation process 1129 can train some parameters of the mathematical model based on the training data for the fasting periods, and train other parameters of the mathematical model based on the other training data from the postprandial periods. Alternatively, or additionally, in some implementations, the mathematical model includes equations that are modified based on the portions of the training data for the fasting periods, and different equations that are modified based on the other portions of training data from the postprandial periods.

The database that is maintained in storage 1128 can store the detected events as labeled events, and different combinations of detected events as labeled event combinations. As described, each labeled event and each labeled event combination can include a label and a probability of an increased insulin delivery demand or a decreased insulin delivery demand for that particular labeled event or that particular combination of detected events. Each labeled event and each labeled event combination can be correlated to a decreased insulin delivery demand; an increased insulin delivery demand; or an ordinary insulin delivery demand. In this embodiment, the database that is maintained in storage 1128 can store and identify the parts of the training data for the fasting periods, the other parts of the training data for the postprandial periods, labeled events and labeled event combinations for the fasting periods, and labeled events and labeled event combinations for the postprandial periods.

In one embodiment of 1210, the adaptation process 1129 can retrieve the training data for the fasting periods, selected ones of the labeled events for the fasting periods, and selected ones of the labeled event combinations for the fasting periods from the database. The adaptation process 1129 can then train the mathematical model 1140 of the user based on the training data for the fasting periods, the selected ones of the labeled events for the fasting periods, and the selected ones of the labeled event combinations for the fasting periods to adapt the mathematical model of the user to identify fasting parameters of a physiological blood glucose response of the user in response to the selected ones of the labeled events for the fasting periods and the selected ones of the labeled event combinations for the fasting periods. For example, the adaptation process 1129 can define parameters of equations of the mathematical model 1140 based on the training data for the fasting periods, the selected ones of the labeled events for the fasting periods, the selected ones of the labeled event combinations for the fasting periods, and other factors such as insulin delivery to the user, to adapt mathematical model of the user to identify fasting parameters of a physiological blood glucose response of the user during fasting periods. Each parameter that is defined based on the training data for the fasting periods is modifiable as a function of one or more of the selected ones of the labeled events for the fasting periods and the selected ones of the labeled event combinations for the fasting periods.

Similarly, the adaptation process 1129 can retrieve the training data for the postprandial periods, selected ones of the labeled events for the postprandial periods, and selected ones of the labeled event combinations for the postprandial periods from the database. The adaptation process 1129 can then train the mathematical model 1140 of the user based on the training data for the postprandial periods, the selected ones of the labeled events for the postprandial periods, and the selected ones of the labeled event combinations for the postprandial periods to adapt the mathematical model of the user to identify fasting parameters of a physiological blood glucose response of the user during the postprandial period in response to the selected ones of the labeled events for the postprandial periods and the selected ones of the labeled event combinations for the postprandial periods. For example, the adaptation process 1129 can define parameters of equations of the mathematical model 1140 based on the training data for the postprandial periods, the selected ones of the labeled events for the postprandial periods, the selected ones of the labeled event combinations for the postprandial periods, and other factors such as carbohydrate intake by the user and insulin delivery to the user, to adapt mathematical model of the user to identify fasting parameters of a physiological blood glucose response of the user during postprandial periods. Each parameter that is defined based on the training data for the postprandial periods is modifiable as a function of one or more of the selected ones of the labeled events for the postprandial periods and the selected ones of the labeled event combinations for the postprandial periods.

Figure 17:
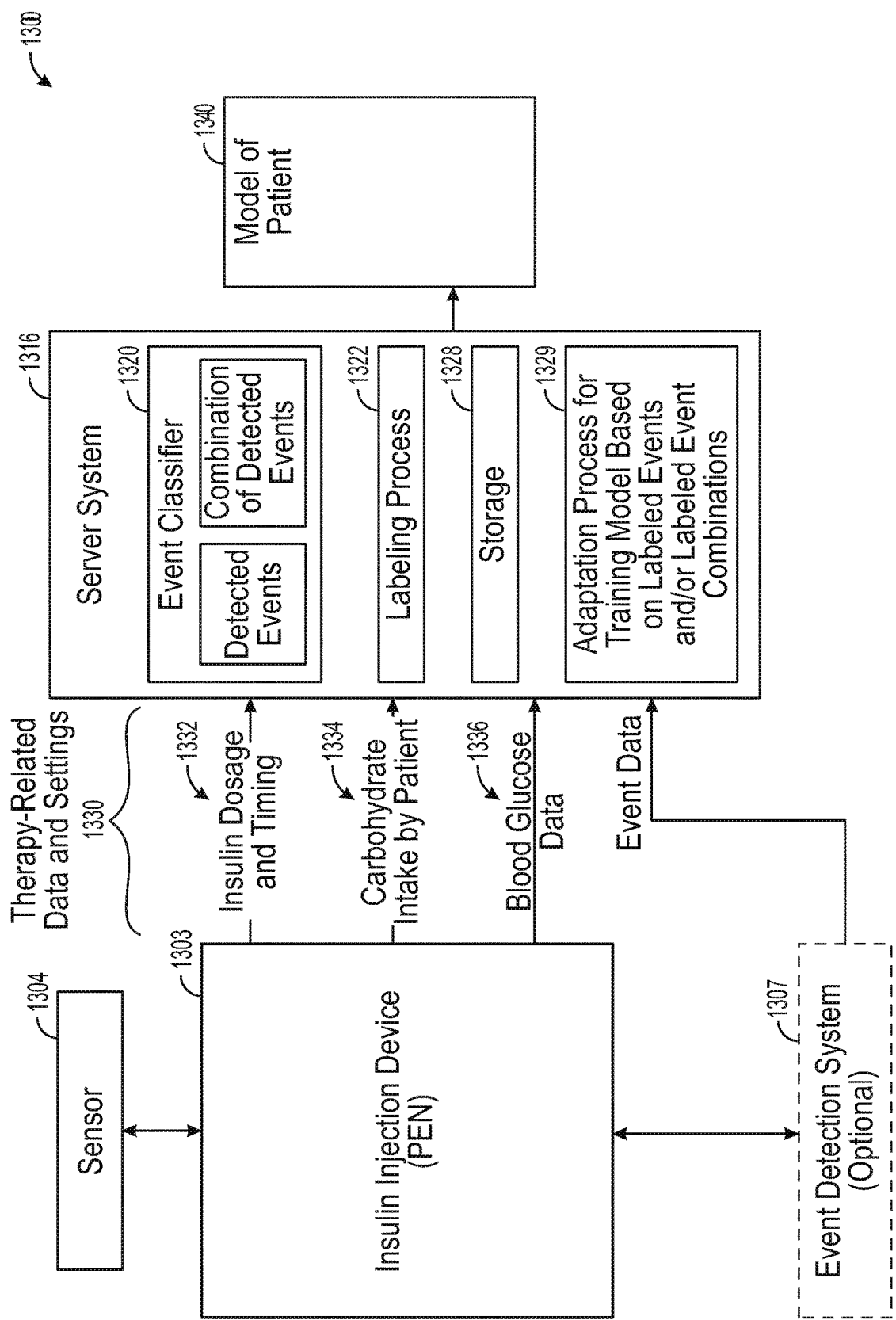
FIG. 17 is a block diagram illustrating another system for training a mathematical model in accordance with certain embodiments.

FIG. 17 is a block diagram illustrating a system 1300 in accordance with certain embodiments. The system 1300 includes a discrete insulin therapy system 1303 having an analyte sensor 1304 associated therewith, an optional event detection system 1307, a server system 1316 and a mathematical model 1340.

The discrete insulin therapy system 1303 can be implemented using any of the discrete insulin therapy system 103 described with respect to FIG. 1, the smart insulin pen 160 described with respect to FIG. 3B, the smart pen accessory 170 described with respect to FIG. 4, the injection pen 200 described with respect to FIG. 5, and/or the insulin infusion device 702 described with respect to FIG. 10. The analyte sensor 1304 used in conjunction with the discrete insulin therapy system 1303 can be implemented using any of the analyte sensor 112 described with respect to FIG. 1, the glucose sensor system 408 described with respect to FIG. 7 and/or a continuous glucose monitoring device of FIG. 9.

The event detection system 1307 can be implemented using any or all components of the event detection system 107 described with respect to FIG. 1, the gesture-based event detection system 500 described with respect to FIG. 8, the gesture-informed patient management system 600 described with respect to FIG. 9, and/or the gesture detection system 704, the activity tracker device 706, and the meal tracking system 708 described with respect to FIG. 10 (and equivalent elements of FIGS. 12 and 15).

The server system 1316 (having an event classifier 1320, a labeling process 1322, storage 1328 and adaptation process 1329) can be implemented using any of the event classification service 111, the database 114 and the data processing system 116 described with respect to FIG. 1, the server system 716 described with respect to FIG. 10, the server system 916 described with respect to FIG. 12, and the server system 1116 described with respect to FIG. 15. The mathematical model 1340 can be implemented using the mathematical models 940, 1140 described with respect to FIGS. 12-16. These devices, systems and models are described with reference to FIGS. 1-16, and for sake of brevity, the description of these devices, systems and models will not be repeated.

The system 1300 of FIG. 17 differs from system 700 of FIG. 10, the system 900 of FIG. 12 and the system 1100 of FIG. 15 in that it utilizes information acquired from the discrete insulin therapy system 1303 to train the mathematical model 1340. As illustrated in the embodiment shown in FIG. 17, the server system 316 can receive training data from the discrete insulin therapy system 1303 of the user. The training data can include therapy-related data and settings 1330 during a period, including but not limited to, data that indicates insulin delivery 1332 to the user during a period, carbohydrate intake 1334 by the user during the period, and blood glucose data 1336 that indicate blood glucose levels of the user during the period. In some examples, server system 1316 obtains carbohydrate intake data 1334 from a user device (e.g., user device 108 of FIG. 1) (not shown in FIG. 17). In some examples, server system 1316 obtains blood glucose data 1336 from another medical device or a user device (e.g., a blood glucose meter and user device 108 of FIG. 1 not shown in FIG. 18). Because the insulin therapy system 1303 is a discrete system, the insulin delivery 1332 to the user during the period can include one or more of data regarding long-acting insulin and data regarding rapid-acting insulin. The data regarding long-acting insulin can include a type of long-acting insulin, a dosage of long-acting insulin, a number of long-acting insulin units to be injected by the user during the period, and timing recommendations for injection of the long-acting insulin units during the period and/or boluses to be injected. The data regarding long-acting insulin can include the type of long-acting insulin, dosage of long-acting insulin (e.g., administered or recommended doses), a number of long-acting insulin units injected or too be injected by the user during the period (e.g., administered or recommended injections), and timing information for the injection of the long-acting insulin units during the period (e.g., timing information for administered or recommended injections). The data regarding rapid-acting insulin can include a type of rapid-acting insulin, a dosage of rapid-acting insulin (e.g., administered or recommended doses), a number of rapid-acting insulin units to be injected by the user during the period during sub-periods of elevated glucose and/or boluses to be injected (e.g., administered or recommended injections), a number of rapid-acting insulin units to be injected by the user before consuming a particular amount of carbohydrates during the period and/or boluses to be injected (e.g., administered or recommended injections), and timing recommendations for injection of the rapid-acting insulin units during the period and/or boluses to be injected (e.g., timing information for administered or recommended injections).

In one embodiment, the therapy-related data and settings 1330 can be directly used to train the mathematical model 1340 that represents physiology of the user. In other words, the event classifier 1320 and labeling process 1322 are not utilized. In such an embodiment, the mathematical model 1340 can be trained based on the training data to generate an adapted mathematical model of the user. The adapted mathematical model of the user simulate a physiological blood glucose response of the user in response to the insulin delivery 1332 to the user and carbohydrate intake 1334 by the user.

In another embodiment, the system 1100 of FIG. 15 can also utilize events and event data acquired from the event detection system 1307 (and various devices and systems thereof) to train the mathematical model 1340, as will now be described below.

In some examples, the event detection system 1307 detects events during the period. Each detected event can be a specific condition or physical activity that is indicative of a physical behavior of the user, as described. The mathematical model 1340 can then be trained based on the training data and at least one of the detected events to generate the adapted mathematical model 1340 of the user that simulates a physiological blood glucose response of the user in response to at least one of the detected events and associated event data. The detected events and event data can be used to train the mathematical model 1340 without processing by the event classifier 1320 and labeling process 1322. For example, based on the training data (e.g., carbohydrate intake 1334 by the user and insulin delivery 1332 to the user) and at least one of the detected events, the adaptation process 1329 can define one or more parameters of equations of the mathematical model 1340 to generate the adapted mathematical model 1340 of the user that simulates a physiological blood glucose response of the user. Each parameter that is defined by the adaptation process 1329 is modifiable as a function of at least one of the detected events.

In some examples, the event classifier 1320 and labeling process 1322 are utilized. Each detected event can include a label and a probability of an increased insulin delivery 1332 demand or a decreased insulin delivery 1332 demand for that detected event as described with reference to FIGS. 12-16. In other words, the event classifier 1320 can correlate each detected event to a decreased insulin delivery demand when the probability of the decreased insulin delivery demand is greater than a first threshold; an increased insulin delivery demand when the probability of the increased insulin delivery demand is greater than a second threshold; or an ordinary insulin delivery demand when the probability of the decreased insulin delivery demand is less than the first threshold and the probability of the increased insulin delivery demand is less than the second threshold. The labeling process 1322 can then add a label to each detected event (or combination of detected events) and associate each detected event (or combination of detected events) with a decreased insulin delivery demand, an increased insulin delivery demand, or an ordinary insulin delivery demand. The adaptation process 1329 can then train the mathematical model 1340 based on the labeled events, and/or the labeled event combinations as described with reference to FIGS. 12-16.

In some cases, an insulin therapy system (e.g., insulin injection device), meal tracking system, medical device, and/or user device may be unavailable (e.g., inaccessible, not in use, etc.) and unable to provide training data for training a mathematical model like those described above. In such case, it would be helpful to use alternative data sources to train the mathematical model.

Figure 18:
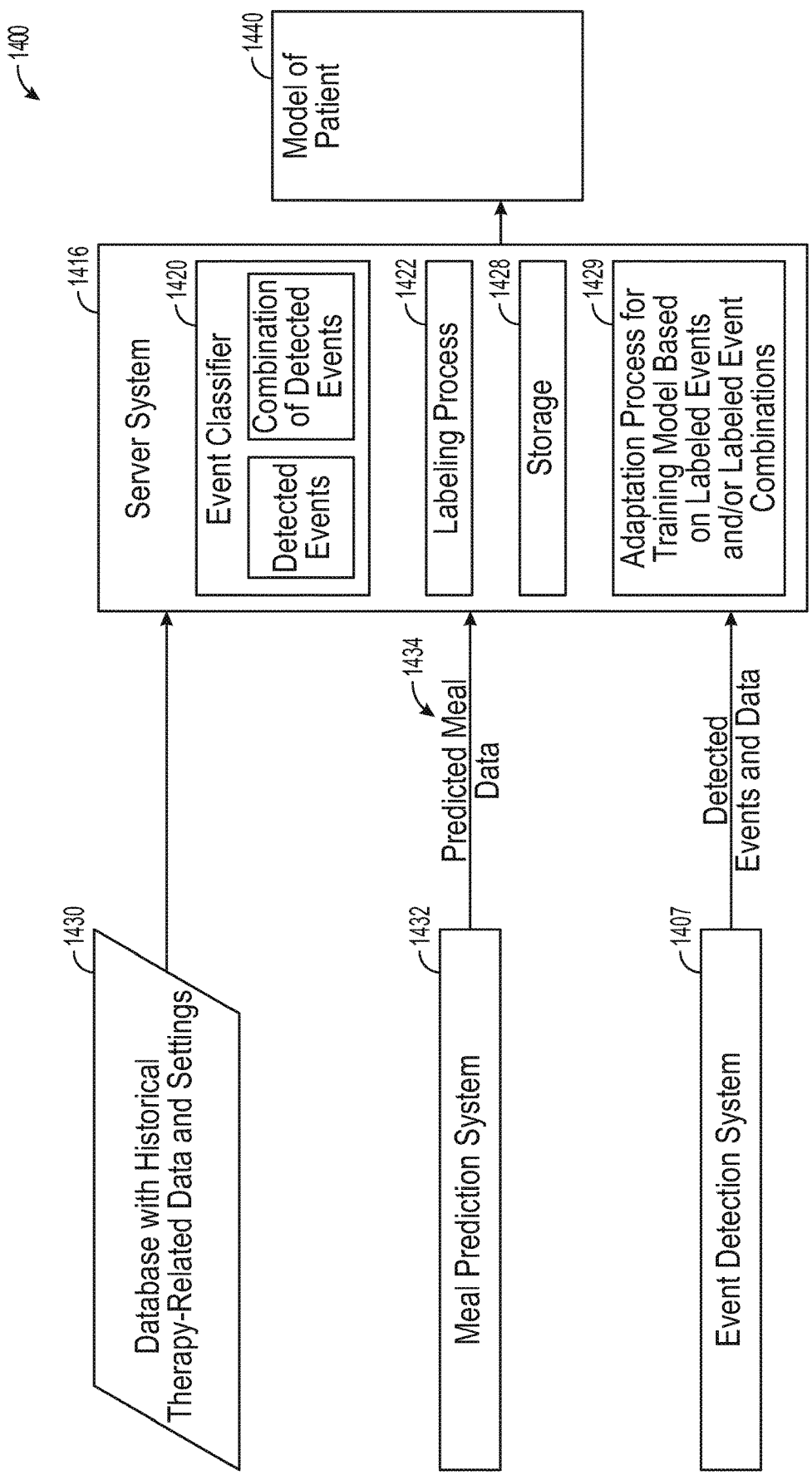
FIG. 18 is a block diagram illustrating another system for training a mathematical model in accordance with certain embodiments.

FIG. 18 is a block diagram illustrating a system 1400 in accordance with certain embodiments. The system 1400 includes a historical database 1430 that stores therapy-related data and settings that were previously acquired from an insulin therapy system of a user, a meal prediction system 1432 that predicts information about meals consumed by the user (referred to as predicted meal data 1434), an optional event detection system 1407, a server system 1416 and a mathematical model 1440.

The event detection system 1407 is optional and can be implemented in some embodiments using any or all components of the event detection system 107 described with respect to FIG. 1, the gesture-based event detection system 500 described with respect to FIG. 8, the gesture-informed patient management system 600 described with respect to FIG. 9, and/or the gesture detection system 704, the activity tracker device 706, and the meal tracking system 708 described with respect to FIG. 10 (and equivalent elements of FIGS. 12 and 15). The server system 1416 can be implemented using any of the database 114 and the data processing system 116 described with respect to FIG. 1, the server system 716 described with respect to FIG. 10, the server system 916 described with respect to FIG. 12, and the server system 1116 described with respect to FIG. 15. Depending on the implementation, the server system 1416 may have an event classifier 1420 (e.g., implemented using the event classification service 111 of FIG. 1), a labeling process 1422, storage 1428 and/or adaptation process 1429. The mathematical model 1440 can be implemented using the mathematical models 940, 1140 described with respect to FIGS. 12-16. These devices, systems and models are described with reference to FIGS. 1-16, and for sake of brevity, the description of these devices, systems and models will not be repeated.

The system 1400 of FIG. 18 differs from system 700 of FIG. 10, the system 900 of FIG. 12 and the system 1100 of FIG. 15 in that system 1400 utilizes information acquired from the historical database 1430 and the meal prediction system 1432 to train the mathematical model 1440. As illustrated in the embodiment shown in FIG. 18, the server system 1416 can receive training data that includes the historical therapy-related data and settings from the historical database 1430 and predicted meal data 1434 from the meal prediction system 1432. The historical therapy-related data and settings from the historical database 1430 can include, but is not limited to, data that indicates insulin delivery to the user during a period, and/or blood glucose data that indicates blood glucose levels of the user during the period. The predicted meal data 1434 can include, but is not limited to, data that indicates a predicted carbohydrate intake by the user during the period.

In some embodiments, the historical therapy-related data and settings from database 1430 and the predicted meal data 1434 can be directly used to train the mathematical model 1440 that represents physiology of the user. In other words, the event classifier 1420 and labeling process 1422 are not utilized. The mathematical model 1440 can be trained based on the historical therapy-related data and settings from the historical database 1430 and predicted meal data 1434 to generate an adapted mathematical model of the user. The adapted mathematical model of the user simulates a physiological blood glucose response of the user in response to the insulin delivery to the user and a predicted carbohydrate intake by the user that can be part of the predicted meal data 1434.

In some embodiments, the system 1100 of FIG. 15 can also utilize events and event data acquired from the event detection system 1407 (and various devices and systems thereof) to train the mathematical model 1440. The event detection system 1407 detects events during the period. Each detected event can be a specific condition or physical activity that is indicative of a physical behavior of the user, as described. The mathematical model 1440 can then be trained based on the historical therapy-related data and settings from the historical database 1430, the predicted meal data 1434 that includes carbohydrate intake by the user, and at least one of the detected events to generate the adapted mathematical model 1440 of the user. The adapted mathematical model 1440 simulates a physiological blood glucose response of the user. In this implementation, the detected events and event data can be used to train the mathematical model 1440 without processing by the event classifier 1420 and labeling process 1422. For example, based on the historical therapy-related data and settings from the historical database 1430, the predicted meal data 1434 (e.g., a predicted carbohydrate intake by the user) and at least one of the detected events, the adaptation process 1429 can define one or more parameters of equations of the mathematical model 1440 to generate the adapted mathematical model 1440 of the user. The adapted mathematical model 1440 simulates a physiological blood glucose response of the user, for example, in response to at least one of the detected events and associated event data. At least some parameters that are defined by the adaptation process 1429 can be modified as a function of one or more of the detected events. The adapted mathematical model 1440 can be made more accurate when information about the user's insulin levels is available (e.g., if the user has an insulin therapy system that can provide data that indicates insulin delivery to the user during a period, and/or blood glucose data that indicates blood glucose levels of the user during the period during a period) and/or meal intake is available (e.g., if the user has meal tracking system available and uses it to enter information about meal(s) they have consumed during a period).

In some examples, the event classifier 1420 and labeling process 1422 can also be implemented so that each detected event or combination of detected events can have a probability associated with it (e.g., a probability of an increased insulin delivery demand for that detected event, a decreased insulin delivery demand for that detected event, or a probability of an ordinary insulin delivery demand for that detected event) and be labeled as described with reference to FIGS. 12-16. In other words, the event classifier 1420 can correlate each detected event to a decreased insulin delivery demand when the probability of the decreased insulin delivery demand is greater than a first threshold; an increased insulin delivery demand when the probability of the increased insulin delivery demand is greater than a second threshold; or an ordinary insulin delivery demand when the probability of the decreased insulin delivery demand is less than the first threshold and the probability of the increased insulin delivery demand is less than the second threshold. The labeling process 1422 can then add a label to each detected event (or combination of detected events) and associate each detected event (or combination of detected events) with a decreased insulin delivery demand, an increased insulin delivery demand, or an ordinary insulin delivery demand. The adaptation process 1429 can then train the mathematical model 1440 based on the historical therapy-related data and settings from database 1430, the predicted meal data 1434, and the labeled event(s) and/or the labeled event combination(s) as described with reference to FIGS. 12-16.

The various tasks performed in connection with a process disclosed herein may be performed by software, hardware, firmware, or any combination thereof. It should be appreciated that an embodiment of an illustrated process may include any number of additional or alternative tasks, the tasks shown in the figures need not be performed in the illustrated order, and a disclosed process may be incorporated into a more comprehensive procedure or process having additional functionality not described in detail herein. Moreover, one or more of the tasks shown in a figure could be omitted from an embodiment of the depicted process as long as the intended overall functionality remains intact.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A processor-implemented method, comprising:
   receiving input data for different combinations of detected events;
   processing each combination of detected events of the different combinations of detected events, the processing comprising:

classifying the combination of detected events using a classifier to map the combination of detected events to a probability of an increased insulin delivery demand or a probability of a decreased insulin delivery demand;

labeling the classified combination of detected events with a label to generate a labeled event combination having the probability of the increased insulin delivery demand or the probability of the decreased insulin delivery demand; and storing the labeled event combination in a database of labeled event combinations;

retrieving, in response to receiving input data for a subsequent combination of detected events, a labeled event combination from the database of labeled event combinations; and controlling, in accordance with the retrieved labeled event combination, an insulin delivery device to adjust insulin delivery by the insulin delivery device.

2. The processor-implemented method according to claim 1, wherein each labeled event combination is correlated to:
a decreased insulin delivery demand when the probability of the decreased insulin delivery demand is greater than a first threshold;
an increased insulin delivery demand when the probability of the increased insulin delivery demand is greater than a second threshold; or
an ordinary insulin delivery demand when the probability of the decreased insulin delivery demand is less than the first threshold and the probability of the increased insulin delivery demand is less than the second threshold.

3. The processor-implemented method according to claim 1, further comprising:
detecting at least some of the detected events using a gesture detection device.

4. The processor-implemented method according to claim 1, wherein at least some of the detected events comprise:
therapy-related data and settings from the insulin delivery device for a user;
meal data comprising predicted carbohydrate intake data for the user;
a specific physical activity performed by the user; or
a combination thereof.

5. The processor-implemented method according to claim 4, wherein the specific physical activity is indicative of a physical behavior of the user and comprises a meal ingestion event, a sleep event, a physical activity event, an exercise event, a work-related event, or a combination thereof.

6. The processor-implemented method according to claim 1, wherein controlling the insulin delivery device comprises:
processing the retrieved labeled event combination to generate one or more therapy parameters for controlling delivery of insulin via the insulin delivery device; and
generating, based on the one or more therapy parameters, recommended settings or commands to control delivery of insulin via the insulin delivery device.

7. The processor-implemented method according to claim 1, wherein controlling the insulin delivery device comprises determining, using a mathematical model,
a physiological blood glucose response of a user of the insulin delivery device in response to the retrieved labeled event combination.

8. The processor-implemented method according to claim 1, further comprising:

tracking events associated with a user that are indicative of physical behavior of the user and correspond to one or more labeled event combinations; and
generating a user interface that provides information indicating an impact of one or more of the tracked events on blood glucose levels of the user and insulin demand of the user.

9. The processor-implemented method according to claim 1, wherein
controlling the insulin delivery device comprises processing the retrieved labeled event combination to generate recommended therapy settings and parameters for calibrating the insulin delivery device.

10. A system, comprising:
one or more processors; and
one or more processor-readable media storing instructions which, when executed by the one or more processors, cause performance of:
receiving input data for different combinations of detected events; and
processing each combination of detected events of the different combinations of detected events to:
classify the combination of detected events using a classifier to map the combination of detected events to a probability of an increased insulin delivery demand or a probability of a decreased insulin delivery demand;
label the classified combination of detected events with a label to generate a labeled event combination having the probability of the increased insulin delivery demand or the probability of the decreased insulin delivery demand; and
store the labeled event combination in a database of labeled event combinations;
retrieving, in response to receiving input data for a subsequent combination of detected events, a labeled event combination from the database of labeled event combinations; and
controlling, in accordance with the retrieved labeled event combination, an insulin delivery device to adjust insulin delivery by the insulin delivery device.

11. The system according to claim 10, wherein each labeled event combination is correlated to:
a decreased insulin delivery demand when the probability of the decreased insulin delivery demand is greater than a first threshold;
an increased insulin delivery demand when the probability of the increased insulin delivery demand is greater than a second threshold; or
an ordinary insulin delivery demand when the probability of the decreased insulin delivery demand is less than the first threshold and the probability of the increased insulin delivery demand is less than the second threshold.

12. The system according to claim 10, further comprising:
a gesture detection device configured to detect at least some of the detected events.

13. The system according to claim 10, wherein at least some of the detected events comprise:
therapy-related data and settings from the insulin delivery device for a user;
carbohydrate intake data for the user;
a specific activity that is indicative of a physical behavior of the user; or
a combination thereof,
wherein the specific activity that is indicative of the physical behavior of the user comprises a meal ingestion event, a sleep event, a physical activity event, an exercise event, a work-related event, or a combination thereof.

14. The system according to claim 10, wherein controlling the insulin delivery device comprises:
processing the retrieved labeled event combination to generate one or more therapy parameters for controlling delivery of insulin via the insulin delivery device; and
generate, based on the one or more therapy parameters, recommended settings or commands to control delivery of insulin via the insulin delivery device.

15. The system according to claim 10, wherein controlling the insulin delivery device comprises determining, using a mathematical model, a physiological blood glucose response of a user of the insulin delivery device in response to the retrieved labeled event combination.

16. The system according to claim 10, wherein the instructions further cause performance of:
tracking events associated with a user that are indicative of physical behavior of the user and correspond to one or more labeled event combinations; and
generating a user interface that provides information indicating an impact of one or more of the tracked events on blood glucose levels of the user and insulin demand of the user.

17. The system according to claim 10, wherein combination to generate recommended therapy settings and parameters for calibrating the insulin delivery device.

18. One or more non-transitory processor-readable media storing instructions which, when executed by one or more processors, cause operations comprising:
receiving input data for different combinations of detected events;
for each combination of detected events of the different combinations of detected events: processing each combination of detected events by:
classifying the combination of detected events using a classifier to map the combination of detected events to a probability of an increased insulin delivery demand or a probability of a decreased insulin delivery demand;
labeling the classified combination of detected events with a label to generate a labeled event combination having the probability of the increased insulin delivery demand or the probability of the decreased insulin delivery demand; and
storing the labeled event combination in a database of labeled event combinations;
retrieving, in response to receiving input data for a subsequent combination of detected events, a labeled event combination from the database of labeled event combinations; and
controlling, in accordance with the retrieved labeled event combination, an insulin delivery device to adjust insulin delivery by the insulin delivery device.

19. The one or more non-transitory processor-readable media according to claim 18, wherein each labeled event combination is correlated to:
a decreased insulin delivery demand when the probability of the decreased insulin delivery demand is greater than a first threshold,
an increased insulin delivery demand when the probability of the increased insulin delivery demand is greater than a second threshold, or
an ordinary insulin delivery demand when the probability of the decreased insulin delivery demand is less than the first threshold and the probability of the increased insulin delivery demand is less than the second threshold.

20. The one or more non-transitory processor-readable media according to claim 18, wherein at least some of the detected events are detected using a gesture detection device; and at least some of the detected events comprise:
therapy-related data and settings from the insulin delivery device for a user;
carbohydrate intake data for the user; and
a specific activity that is indicative of a physical behavior of the user,
wherein the specific activities that are indicative of the physical behavior of the user comprise one or more of: a meal ingestion event, a sleep event, a physical activity event, an exercise event and a work-related event.

* * * * *